United States Patent
Hellerbrand et al.

(10) Patent No.: US 9,907,829 B2
(45) Date of Patent: *Mar. 6, 2018

(54) STABLE MIA/CD-RAP FORMULATION

(71) Applicant: Scil Technology GmbH, Martinsried (DE)

(72) Inventors: Klaus Hellerbrand, Moorenweis (DE); Rainer Sigl, Puchheim (DE)

(73) Assignee: SCIL TECHNOLOGY GMBH, Martinsried (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/336,155

(22) Filed: Oct. 27, 2016

(65) Prior Publication Data

US 2017/0042971 A1 Feb. 16, 2017

Related U.S. Application Data

(63) Continuation of application No. 13/661,743, filed on Oct. 26, 2012, now Pat. No. 9,511,116, which is a continuation of application No. PCT/EP2011/056622, filed on Apr. 27, 2011.

(30) Foreign Application Priority Data

Apr. 27, 2010 (EP) .................................... 10161160

(51) Int. Cl.
| | |
|---|---|
| *A61K 38/00* | (2006.01) |
| *A61K 38/16* | (2006.01) |
| *A61K 38/17* | (2006.01) |
| *A61K 9/00* | (2006.01) |
| *A61K 47/22* | (2006.01) |
| *C07K 14/47* | (2006.01) |
| *C07K 14/78* | (2006.01) |
| *A61K 47/24* | (2006.01) |

(52) U.S. Cl.
CPC ........ *A61K 38/1709* (2013.01); *A61K 9/0019* (2013.01); *A61K 47/22* (2013.01); *A61K 47/24* (2013.01); *C07K 14/4703* (2013.01); *C07K 14/78* (2013.01); *A61K 9/0024* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,244,943 A | 1/1981 | Yamahira et al. | |
| 4,374,763 A | 2/1983 | Takagi | |
| 5,580,856 A | 12/1996 | Prestrelski et al. | |
| 5,770,366 A | 6/1998 | Bogdahn et al. | |
| 5,919,443 A * | 7/1999 | Michaelis | A61K 9/0019 424/85.1 |
| 6,583,272 B1 | 6/2003 | Bailon | |
| 9,511,116 B2 * | 12/2016 | Hellerbrand | A61K 9/0019 |
| 2002/0009493 A1 | 1/2002 | Schwendeman et al. | |
| 2002/0103360 A1 | 8/2002 | Pan et al. | |
| 2003/0091583 A1 | 5/2003 | Hubert et al. | |
| 2003/0180287 A1 | 9/2003 | Gombotz et al. | |
| 2003/0202972 A1 | 10/2003 | Andya et al. | |
| 2005/0020498 A1 | 1/2005 | Flores et al. | |
| 2009/0060906 A1 | 3/2009 | Barry et al. | |

FOREIGN PATENT DOCUMENTS

| | | |
|---|---|---|
| EP | 0 315 968 A1 | 5/1989 |
| WO | 01/55332 A2 | 8/2001 |
| WO | 2004/015078 A2 | 2/2004 |
| WO | 2007/109221 A2 | 9/2007 |
| WO | 2008/040556 A1 | 4/2008 |
| WO | 2008/040557 A1 | 4/2008 |

OTHER PUBLICATIONS

Schmid et al. (2010, Cell Death and Disease 1: 1-10).
Lougheed, J.C., et al. (2002) "Solution structure and dnamics of melanoma inhibitory activity protein", Journal of Biomoelecular NMR 22: pp. 211-223.
Shiraki et al. (2004, Eur. J. Biochem. 271: 3242-3247).
Arakawa et al. (2003, Biochem. Biophys. Res. Commun. 3404: 148-152).
PCT Search Report International Application No. PCT/EP2011/056622; dated Apr. 11, 2012.
Arakawa T., et al., (2007) Suppression of protein interactions by arginine: A proposed mechanism of the arginine effects, Biophysical Chemistry 127: 1-8.
Schubert T., et al., (2010) Modulation of cartilage differentiation by melanoma inhibiting activity/cartilage-derived retinoic acid-sensitive protein (MIA/CD-RAP), Experimental and Molecular Medicine 42: 166-174.

* cited by examiner

Primary Examiner — Elizabeth C. Kemmerer
(74) Attorney, Agent, or Firm — Kagan Binder, PLLC

(57) ABSTRACT

The present invention relates to stable aqueous formulations comprising at least 5 mg/mL CD-RAP and a charged amino acid, said amino acid preferably having a net charge at a pH between about 6 and 8. The ingredients of the formulation preferably provide stability over repeated freeze-thaw cycles. In a preferred aspect, the formulation is for use in therapy, preferably for use in the treatment of inflammatory disorders, preferably osteoarthritis. Furthermore, a kit comprising the formulation of the invention is provided.

16 Claims, 11 Drawing Sheets

SEQUENCE LISTING

```
<160> NUMBER OF SEQ ID NOS: 6

<210> SEQ ID NO 1
<211> LENGTH: 107
<212> TYPE: PRT
<213> ORGANISM: Homo sapiens

<400> SEQUENCE: 1

Gly Pro Met Pro Lys Leu Ala Asp Arg Lys Leu Cys Ala Asp Gln Glu
1               5                   10                  15

Cys Ser His Pro Ile Ser Met Ala Val Ala Leu Gln Asp Tyr Met Ala
            20                  25                  30

Pro Asp Cys Arg Phe Leu Thr Ile His Arg Gly Gln Val Val Tyr Val
        35                  40                  45

Phe Ser Lys Leu Lys Gly Arg Gly Arg Leu Phe Trp Gly Gly Ser Val
    50                  55                  60

Gln Gly Asp Tyr Tyr Gly Asp Leu Ala Ala Arg Leu Gly Tyr Phe Pro
65                  70                  75                  80

Ser Ser Ile Val Arg Glu Asp Gln Thr Leu Lys Pro Gly Lys Val Asp
                85                  90                  95

Val Lys Thr Asp Lys Trp Asp Phe Tyr Cys Gln
            100                 105

<210> SEQ ID NO 2
<211> LENGTH: 98
<212> TYPE: PRT
<213> ORGANISM: Artificial
<220> FEATURE:
<223> OTHER INFORMATION: generic human CD-RAP sequence
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(23)
<223> OTHER INFORMATION: Xaa can be any naturally occurring amino acid
<220> FEATURE:
<221> NAME/KEY: misc_feature
<222> LOCATION: (25)..(36)
<223> OTHER INFORMATION: Xaa can be any naturally occurring amino acid
<220> FEATURE:
<221> NAME/KEY: misc_feature
<222> LOCATION: (38)..(50)
<223> OTHER INFORMATION: Xaa can be any naturally occurring amino acid,
```

```
       wherein the number of any naturally occurring amino acid may vary
       from 11-13
<220> FEATURE:
<221> NAME/KEY: misc_feature
<222> LOCATION: (52)..(69)
<223> OTHER INFORMATION: Xaa can be any naturally occurring amino acid,
       wherein the number of any naturally occurring amino acid may vary
       from 7-18
<220> FEATURE:
<221> NAME/KEY: misc_feature
<222> LOCATION: (71)..(74)
<223> OTHER INFORMATION: Xaa can be any naturally occurring amino acid
<220> FEATURE:
<221> NAME/KEY: misc_feature
<222> LOCATION: (76)..(96)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid

<400> SEQUENCE: 2

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Cys Xaa Xaa Xaa Xaa Xaa Xaa Xaa
            20                  25                  30

Xaa Xaa Xaa Xaa Val Xaa Xaa Xaa Xaa Xaa Xaa Xaa Xaa Xaa Xaa
        35                  40                  45

Xaa Xaa Trp Xaa Xaa Xaa Xaa Xaa Xaa Xaa Xaa Xaa Xaa Xaa Xaa
    50                  55                  60

Xaa Xaa Xaa Xaa Xaa Phe Xaa Xaa Xaa Xaa Val Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Cys Xaa

<210> SEQ ID NO 3
<211> LENGTH: 100
<212> TYPE: PRT
<213> ORGANISM: Artificial
<220> FEATURE:
<223> OTHER INFORMATION: generic human CD-RAP sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(19)
<223> OTHER INFORMATION: Xaa can be any naturally occurring amino acid
<220> FEATURE:
<221> NAME/KEY: misc_feature
<222> LOCATION: (21)..(23)
<223> OTHER INFORMATION: Xaa can be any naturally occurring amino acid
<220> FEATURE:
<221> NAME/KEY: misc_feature
<222> LOCATION: (27)..(38)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid
<220> FEATURE:
```

```
<221> NAME/KEY: misc_feature
<222> LOCATION: (44)..(52)
<223> OTHER INFORMATION: Xaa can be any naturally occurring amino acid,
      wherein the number of any naturally occurring amino acid may vary
      from 7-9
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (57)..(69)
<223> OTHER INFORMATION: Xaa can be any naturally occurring amino acid,
      wherein the number of any naturally occurring amino acid may vary
      from 5-13
<220> FEATURE:
<221> NAME/KEY: misc_feature
<222> LOCATION: (74)..(76)
<223> OTHER INFORMATION: Xaa can be any naturally occurring amino acid
<220> FEATURE:
<221> NAME/KEY: misc_feature
<222> LOCATION: (78)..(95)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid

<400> SEQUENCE: 3

Lys Xaa Cys Xaa Asp Xaa Glu Cys Xaa Xaa Xaa Xaa Xaa Xaa Xaa
1               5                   10                  15

Xaa Xaa Xaa Asp Xaa Xaa Xaa Pro Asp Cys Xaa Xaa Xaa Xaa Xaa
            20                  25                  30

Xaa Xaa Xaa Xaa Xaa Xaa Val Xaa Xaa Lys Leu Xaa Xaa Xaa Xaa Xaa
        35                  40                  45

Xaa Xaa Xaa Xaa Trp Xaa Gly Ser Xaa Xaa Xaa Xaa Xaa Xaa Xaa
    50                  55                  60

Xaa Xaa Xaa Xaa Xaa Gly Tyr Phe Pro Xaa Xaa Xaa Val Xaa Xaa Xaa
65                  70                  75                  80

Xaa Xaa Xaa Xaa Xaa Xaa Xaa Xaa Xaa Xaa Xaa Xaa Xaa Xaa Asp
            85                  90                  95

Phe Xaa Cys Xaa
            100

<210> SEQ ID NO 4
<211> LENGTH: 98
<212> TYPE: PRT
<213> ORGANISM: Artificial
<220> FEATURE:
<223> OTHER INFORMATION: generic human CD-RAP sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(16)
<223> OTHER INFORMATION: Xaa can be any naturally occurring amino acid
<220> FEATURE:
```

```
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(23)
<223> OTHER INFORMATION: Xaa can be any naturally occurring amino acid
<220> FEATURE:
<221> NAME/KEY: misc_feature
<222> LOCATION: (29)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(41)
<223> OTHER INFORMATION: Xaa can be any naturally occurring amino acid
<220> FEATURE:
<221> NAME/KEY: misc_feature
<222> LOCATION: (44)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (56)..(67)
<223> OTHER INFORMATION: Xaa can be any naturally occurring amino acid
<220> FEATURE:
<221> NAME/KEY: misc_feature
<222> LOCATION: (72)..(93)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid

<400> SEQUENCE: 4

Lys Xaa Cys Xaa Asp Xaa Xaa Cys Xaa Xaa Xaa Xaa Xaa Xaa Xaa
1               5                   10                  15

Ala Xaa Xaa Asp Xaa Xaa Xaa Pro Asp Cys Arg Phe Xaa Xaa Xaa Xaa
            20                  25                  30

Xaa Gly Xaa Val Xaa Xaa Xaa Xaa Xaa Lys Leu Xaa Xaa Xaa Xaa Xaa
        35                  40                  45

Xaa Xaa Trp Xaa Gly Ser Val Xaa Xaa Xaa Xaa Xaa Xaa Xaa Xaa Xaa
    50                  55                  60

Xaa Xaa Xaa Gly Tyr Phe Pro Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Asp Phe Xaa
                85                  90                  95

Cys Gln

<210> SEQ ID NO 5
<211> LENGTH: 22
<212> TYPE: DNA
<213> ORGANISM: Artificial
<220> FEATURE:
<223> OTHER INFORMATION: primer sequence for human MMP-13 gene

<400> SEQUENCE: 5
gggttcctga tgtgggtgaa ta                                           22

<210> SEQ ID NO 6
<211> LENGTH: 19
<212> TYPE: DNA
<213> ORGANISM: Artificial
```

```
<220> FEATURE:
<223> OTHER INFORMATION: primer sequence for human MMP-13 gene

<400> SEQUENCE: 6
gccatcgtga agtctggta                                              19
```

STABLE MIA/CD-RAP FORMULATION

Figure 1:
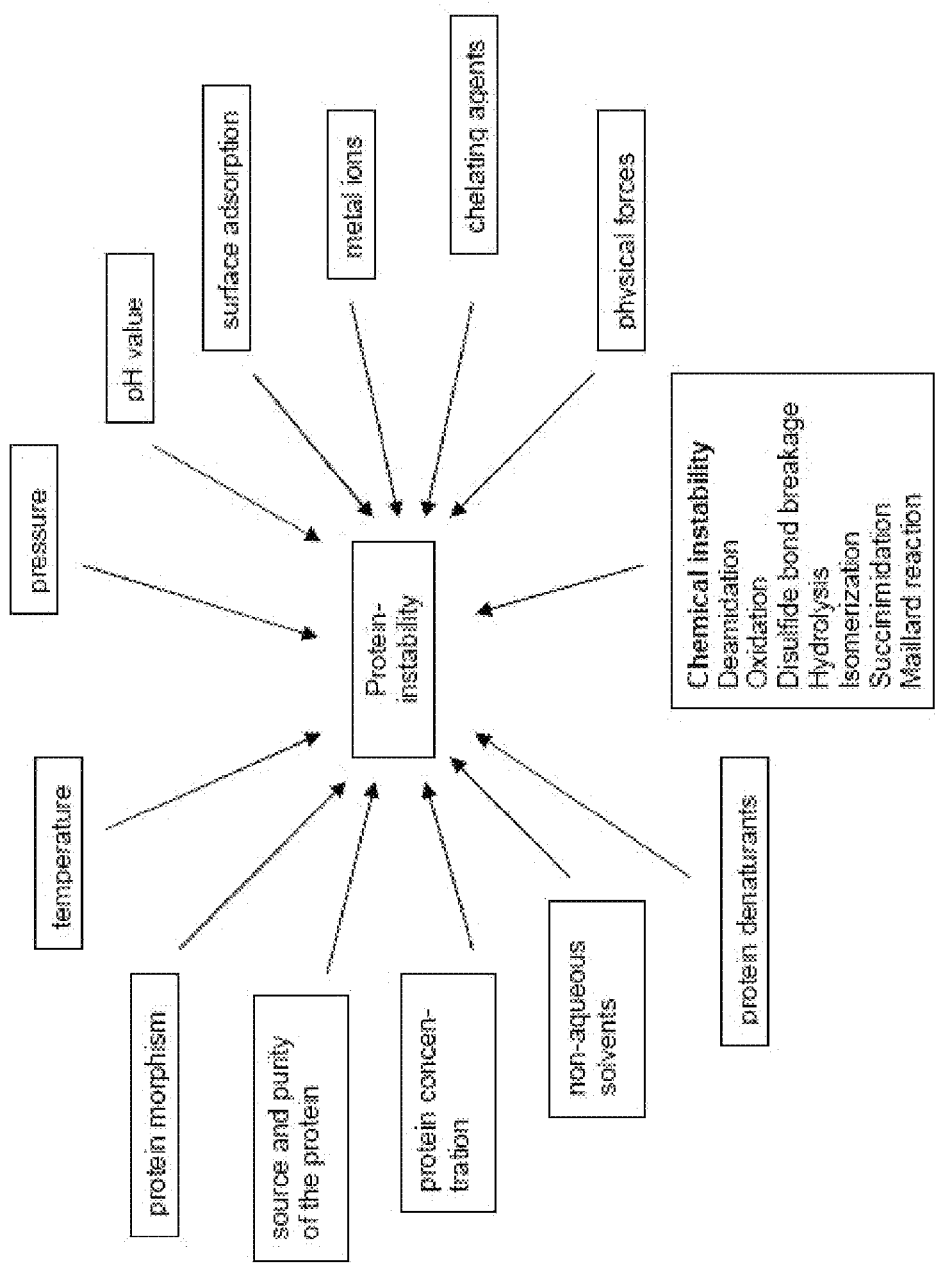

This application is a continuation of U.S. patent application Ser. No. 13/661,743, filed Oct. 26, 2012, now U.S. Pat. No. 9,511,116, issued Dec. 6, 2016, which is a continuation of International Application No. PCT/EP2011/056622, which was filed on Apr. 27, 2011, which in turn claims priority to EP Application No. 10161160.6, on Apr. 27, 2010; wherein the entireties of said patent applications are incorporated herein by reference. Also, the entire contents of the ASCII text file entitled "IPM0033US_Sequence_Listen-2.txt" created on Dec. 21, 2012, having a size of 9 kilobytes is incorporated herein by reference.

The present invention relates to stable aqueous formulations comprising at least 5 mg/mL CD-RAP and a charged amino acid, said amino acid preferably having a net charge at a pH between about 6 and 8. The ingredients of the formulation preferably provide stability over repeated freeze-thaw cycles. In a preferred aspect, the formulation is for use in therapy, preferably for use in the treatment of inflammatory disorders, preferably osteoarthritis. Furthermore, a kit comprising the formulation of the invention is provided.

Proteins are used in a wide range of applications in the fields of pharmaceuticals, veterinary products, cosmetics and other consumer products, foods, feeds, diagnostics, industrial chemistry and decontamination. At times, such uses have been limited by constraints inherent in proteins themselves or imposed by the environment or media in which they are used. Such constraints may result in poor stability of the proteins, variability of performance or high cost. Due to the advent of biotechnology it is possible to produce a wide variety of proteins for therapeutic applications. After their production, protein pharmaceuticals are usually stored prior to their use. Due to the fact that proteins are generally larger and more complex than "traditional" pharmaceuticals, formulation and processing of protein pharmaceuticals that are suitable for storage can be particularly challenging. For reviews of protein pharmaceutical formulation and process design, see Carpenter et al. (1997), Pharm. Res. 14:969-975; Wang (2000), Int. J. Pharmaceutics 203:1-60; and Tang and Pikal (2004), Pharm. Res. 21:191-200.

Several factors can be considered in designing formulations and processes for protein pharmaceutical production. Of primary concern is the stability of the protein through any or all steps of manufacture, shipping, and handling steps, which may include preparation of the composition, freezing, drying, storage, shipping, reconstitution, freeze/thaw cycles, and post-reconstitution storage by the end user. Other potential considerations include ease and economy of manufacture, handling, and distribution; composition of the final product for patient administration; and ease of use by the end user, including solubility of the lyophilized formulation upon reconstitution.

Liquid formulations may satisfy certain objectives. Possible advantages of liquid formulations include ease and economy of manufacture and convenience for the end user. Frequently, when stored for extended periods polypeptides are unstable in solution (Manning et al (1989), Pham. Res. 6: 903-918). Accordingly, additional processing steps have been developed to allow for a longer shelf life including drying, e. g., lyophilization. Lyophilized formulations may also provide certain advantages. Potential benefits of lyophilization include improved protein stability as well as ease and economy of shipping and storage. However, lyophilized pharmaceutical compositions may be less convenient for the end user.

In addition to the choice of the basic form of the composition (e.g., lyophilized, liquid, frozen, etc.), optimization of a protein formulation typically involves varying the components of the formulation and their respective concentrations to maximize protein stability. A variety of factors may affect protein stability, including ionic strength, pH, temperature, freeze/thaw cycles, shear forces, freezing, drying, agitation, and reconstitution. Protein instability may be caused by physical degradation (e.g., denaturation, aggregation, or precipitation) or chemical degradation (e.g., deamidation, oxidation, or hydrolysis). Optimization of formulation components and concentrations is solely based on empirical studies and/or rational approaches to overcoming sources of instability.

Sometimes, in long-term storage of pharmaceutical compositions containing polypeptides, including aqueous and lyophilized formulations, active polypeptides can be lost due to aggregation and/or degradation.

Accordingly, typical practices to improve polypeptide stability can be addressed by varying the concentration of elements with the formulation, or by adding excipients to modify the formulation (U.S. Pat. Nos. 5,580,856 and 6,171,586 and U.S. Patent application Nos. US 2003/0202972, US 2003/0180287). U.S. Pat. No. 5,580,856 is a prototype application of which agents could be added to stabilize a dried protein during or after rehydration such as natural polymers, surfactants, sulfated polysaccharides, proteins and buffers. However, apart from many options, U.S. Pat. No. 5,580,856 does not teach which rehydration stabilizer should be added for which protein. Accordingly, while the skilled reader is made aware of that many options, he or she would have to find out for his/her protein the best conditions among the many options described by U.S. Pat. No. 5,580,856. US patent application 2003/0202972 describes a stable lyophilized formulation of an anti-Her2 antibody, wherein the stabilizer is sugar, trehalose, or a buffer. Yet, while these stabilizers may be useful for an antibody, they cannot be extrapolated to other proteins. US patent application 2003/0180287 is similar to US 2003/0202972 in that it also describes a stable solution of an immunoglobulin-like protein, i.e., a protein containing an Fc domain. The stabilizer may be sodium phosphate, potassium phosphate, sodium or potassium citrate, maleic acid, ammonium acetate, trisbuffer, acetate, diethaolamine, histidine, lysine or cysteine. Among these chemically distinct stabilizers which could be chosen by the skilled reader, lysine turned out to be suitable. However, like with US 2003/0202972, the specific stabilizer is merely suitable for a specific protein, here an Fc domain containing protein, and cannot per se be extrapolated to another protein. Accordingly, the use of additives cannot be extrapolated from a specific protein to another un-related protein. Indeed, the use of additives—while improving storage—can still results in inactive polypeptides. In addition, in the case of lyophilization, the rehydration step can introduce conditions that result in inactivation of the polypeptide by, for example, aggregation or denaturation (Hora et al. (1992), Pharm. Res., 9: 33-36; Liu et al. (1991), Biotechnol. Bioeng., 37: 177-184). In fact, aggregation of polypeptides is undesirable as it may result in immunogenicity (Cleland et al. (1993), Crit. Rev. Therapeutic Drug Carrier Systems, 10: 307-377; and Robbins et al. (1987), Diabetes, 36: 838-845).

Maintenance of biological activity during the development and manufacture of pharmaceutical products depends on the inherent stability of the macromolecule, as well as the stabilization techniques employed. A range of protein stabilization techniques exist; including addition of chemical-"stabilizers" to the aqueous solution or suspension of protein. For example, U.S. Pat. No. 4,297,344 discloses stabilization of coagulation factors II and VIII, antithrombin III and plasminogen against heat by adding selected amino acids. U.S. Pat. No. 4,783,441 discloses a method for stabilizing proteins by adding surface-active substances. U.S. Pat. No. 4,812,557 discloses a method for stabilizing interleukin-2 using human serum albumin. Freeze/thaw methods in which the preparation is mixed with a cryoprotectant and stored at very low temperatures is another option to stabilize a protein. However, not all proteins will survive a freeze/thaw cycle. Cold storage with cryoprotectant additive, normally glycerol is a further option. Storage in the glass form, as described in U.S. Pat. No. 5,098,893 could also be made. In this case, proteins are dissolved in water-soluble or water-swellable substances which are in amorphous or glassy state. The most widely used method for the stabilization of proteins is freeze-drying or lyophilisation. Whenever sufficient protein stability cannot be achieved in aqueous solution, lyophilization provides the most viable alternative. One disadvantage of lyophilization is that it requires sophisticated processing, is time consuming and expensive. In addition, if lyophilization is not carried out carefully, most preparations are at least partially denatured by the freezing and dehydration steps of the technique. The result is frequently irreversible aggregation of a portion of protein molecules, rendering a formulation unacceptable for parenteral administration.

Generally spoken, the degradation of proteins has been well described in the literature, but the storage and solubility, in particular, of CD-RAP/MIA (further referred to as CD-RAP) has not been described. CD-RAP is a small, soluble protein secreted from malignant melanoma cells and from chondrocytes. Recent evidence has identified CD-RAP as the prototype of a small family of extracellular proteins adopting an SH3 domain-like fold. It is thought that interaction between CD-RAP and specific epitopes in extracellular matrix proteins regulates the attachment of tumor cells and chondrocytes (Moser et al. (2002), Mol Cell Biol. 5:1438-45). Meanwhile, CD-RAP-related proteins are known from US 2002/0103360 and WO 2004/015078. However, both applications are silent about stable formulations of the CD-RAP-related proteins, Thus far, a liposome-based formulation of CD-RAP is known from WO 2008/040556. Specifically, a dried pharmaceutical composition comprising large multilamellar vesicles containing CD-RAP after reconstitution is disclosed, whereby the CD-RAP protein is encapsulated and/or entrapped in liposomes for sustained CD-RAP delivery such that it can remain for a longer period of time at the desired site of action.

One function of CD-RAP is that it acts as a chemotactic factor on mesenchymal stem cells. While, CD-RAP is not capable of inducing the differentiation of murine or human mesenchymal stem cells (HMSC), it influences the action of bone morphogenetic protein (BMP)-2 and transforming growth factor (TGF)-beta 3 during mesenchymal stem cell differentiation, supporting the chondrogenic phenotype while inhibiting osteogenic differentiation. Further, CD-RAP down-regulates gene expression of osteopontin and osteocalcin in BMP-2 treated HMSC cultures inhibiting the osteogenic potential of BMP-2. In the case of human primary chondrocytes CD-RAP stimulates extracellular matrix deposition, increasing the glycosaminoglycan content.

Therefore, it is believed that CD-RAP is an important regulator during chondrogenic differentiation and maintenance of cartilage. Accordingly, CD-RAP is believed to be a promising candidate for cartilage repair. It would therefore be desirable to have available pharmaceutical formulations comprising CD-RAP in a sufficiently high amount which is stable over a prolonged time during storage. In fact, stable formulations with high concentrations of CD-RAP would enable lower volume injections for patients, which reduces side effects like pain due to high volume injection and allows naturally the increase of each dose.

In addition, while it was known in the art that a multitude of options of protein stabilizing agents as well as agents which allow a high concentration of a protein while being kept stable were available, up to the present invention, it was not recognized in the art that a formulation comprising a CD-RAP protein in high concentrations could be unstable and thus require improvement.

Hence, the technical problem of the present invention is to comply with the needs described above.

The present invention addresses these needs and thus provides as a solution to the technical problem the embodiments concerning formulations as well as methods and uses applying these formulations in the treatment of subjects suffering from diseases which would benefit from the administration of CD-RAP. These embodiments are characterized and described herein, illustrated in the Examples, and reflected in the claims.

It must be noted that as used herein, the singular forms "a", "an", and "the", include plural references unless the context clearly indicates otherwise. Thus, for example, reference to "an antibody" includes one or more of such different antibodies and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present inventors with the aim of providing a formulation which has a high amount of CD-RAP in order to enable lower volume when being injected into subjects in need thereof so as to reduce side effects like pain due to high volume injection recognized that a CD-RAP protein may be unstable at high concentrations and may also be unstable over a prolonged period of storage.

That being so, the present inventors have observed certain instability of CD-RAP proteins during their studies with the aim of providing a highly concentrated, stable formulation and, thus, aimed at improving this undesired observation. Accordingly, they aimed at concentrating CD-RAP while keeping it in solution, i.e., in a dissolved stage. In doing so, they had a multitude of options and alternatives available, without, however, any indication that any of them would be suitable to solve the objective problem.

"Dissolved stage" means that the CD-RAP protein, preferably in a concentration of at least 5 mg/ml CD-RAP, is in solution, i.e., (dis)solved and/or dispersed directly in the aqueous solution (i.e., in the aqueous phase) of the formulation. Preferably, the CD-RAP protein is homogenously (dis)solved and/or dispersed. Homogenously means that the amount of CD-RAP protein that is (dis)solved and/or dispersed in the stable aqueous formulation is nearly evenly, preferably evenly, distributed in the aqueous formulation so that the concentration ("c") of the amount of CD-RAP protein ("n" in case of molar mass or "m" in case of mass) is nearly identical, preferably identical in (or throughout) the volume ("v") of the aqueous solution, i.e., $c=n/v$ or $c=m/v$, respectively, is nearly constant, preferably constant. Preferably there is no concentration gradient within the formulation.

Accordingly, the stable aqueous formulation of the present invention comprising a CD-RAP protein can preferably be regarded as an aqueous solution, wherein a CD-RAP is directly dissolved and/or dispersed therein.

More preferably, the stable aqueous formulation of the present invention can be regarded as an aqueous at least 5 mg/ml CD-RAP protein and a charged amino acid. This means that the formulation is based on an aqueous solution, wherein at least 5 mg/ml CD-RAP protein is dissolved and/or dispersed together with at least the charged amino acid.

Alternatively, the stable aqueous formulation of the present invention can be more preferably regarded as a stable formulation based on an aqueous solution, the formulation comprising at least a concentration (weight/volume) of 5 mg/ml CD-RAP protein and a charged amino acid.

A "solution" is a homogenous mixture of one or two or more substances/components. In such a mixture, a solute (in the present invention a CD-RAP protein, preferably at least 5 mg/ml CD-RAP protein) is dissolved (as described above) in another substance (in the present invention preferably an aqueous formulation), also known as solvent.

Given the above, the CD-RAP protein is preferably not heterogeneously dissolved and/or dispersed in the aqueous solution. The term "dissolved state" also includes that the CD-RAP protein is preferably essentially not emulsified, or more preferably not emulsified at all in the aqueous solution.

Also, the term "dissolved state" includes that the CD-RAP protein is preferably not essentially encapsulated and/or entrapped (preferably less than 2%, 1%, or 0.5% of the CD-RAP protein may be encapsulated and/or entrapped), or more preferably not encapsulated and/or entrapped at all, e.g., in liposomes, multilamellar liposomes or the like.

Accordingly, in a preferred aspect, the present invention encompasses a stable aqueous essentially liposome free (preferably less than 2%, 1%, or 0.5% liposomes), preferably liposome free, formulation comprising at least 5 mg/ml CD-RAP protein and a charged amino acid.

In an alternative more preferred aspect, the present invention encompasses a stable aqueous formulation comprising at least 5 mg/ml CD-RAP protein and a charged amino acid, wherein the CD-RAP protein is essentially not contained (preferably less than 2, 1, or 0.5%), preferably not contained (encapsulated and/or entrapped) in liposomes.

Indeed, there are many ways a protein can be unstable. For example, protein instability could be caused by protein aggregation, but also by chemical instability due to deamination, oxidation, disulfide bond breakage and formation, hydrolysis, succinimidation, non-disulfide crosslinking, deglycosylation or "enzymatic browning" (Maillard reaction) or any combination of these phenomena; see, for example, Wang et al. (1999), Int. J. Pharm. 185: 129-188) and FIG. 1. Furthermore, physicochemical parameters such as the temperature, pH value, surface adsorption, salts, metal ions, chelating agents, physical forces such as shear forces, protein denaturants, non-aqueous solvents, protein concentration, source and purity of the protein, protein morphism or pressure can influence protein stability.

Yet, that many factors which can influence protein stability that many measures could be taken to stabilize a protein. For example, a protein can be internally (by changing amino acids) or externally stabilized. External stabilization could be achieved by chelating agents, metal ions, reducing agents, polymers, polyethylene glycols/polyols, serum albumin, surfactants, sugars and polyols, fatty acids and phospholipids, amino acids, buffers, etc.; see, for example, Wang, Y and Hanson M (1988), J. Parental Sci. & Technology, 42, Supplement: 4-26; Wang et al. (1999), Int. J. Pharm. 185: 129-188, and FIG. 2. In sum, for stabilizing a CD-RAP protein in a formulation, the skilled person would have had many options available.

In the present case, the inventors observed that the CD-RAP protein showed aggregation. Many different factors can cause the aggregation of a protein in a protein formulation. Typical purification and storage procedures can expose protein formulations to conditions and components that cause the protein to aggregate. For example, proteins in a protein formulation may aggregate as a result of any one or more of the following: storage, exposure to elevated temperatures, the pH of the formulation, the ionic strength of the formulation, and the presence of certain surfactants (e.g., polysorbate-20 and polysorbate-80) and emulsifying agents. Similarly, proteins may aggregate when exposed to shear stress, such as, reconstituting a lyophilized protein cake in solution, filter-purifying a protein sample, freeze-thawing, shaking, or transferring a protein solution via syringe. Aggregation can also occur as a result of interactions of polypeptide molecules in solution and at the liquid-air interfaces within storage vials. Conformational changes may occur in polypeptides adsorbed to air-liquid and solid-liquid interfaces during compression or extension of the interfaces resulting from agitation during transportation. Such agitation can cause the protein of a formulation to aggregate and ultimately precipitate with other adsorbed proteins.

In addition, exposure of a protein formulation to light can cause the protein to aggregate. The present invention thus provides formulations whichenable high concentrations of CD-RAP and which reduce aggregation of proteins. Without being bound by theory the reduction of protein aggregation is achieved by controlling one or more of the above-mentioned aggregation mechanisms. This can result in, for example, improved product stability, and greater flexibility in manufacturing processes and storage conditions.

Specifically, the present inventors found that out of many tested agents amino acids which carry a net charge at a pH between about 6 and about 8 are useful to stabilize a CD-RAP protein at a high concentration by, inter alia, mediating protein solubility and/or inhibiting protein aggregation. When referred herein an amino acid is preferably meant to be an L-amino acid. Less preferred is a D-amino acid. Preferably the amino acid is L-histidine, L-arginine, L-glutamic acid or a salt thereof; preferably the salt is a chloride, phosphate, acetate or sulfate.

Accordingly, the invention is based, at least in part, on the discovery that formulations comprising at least 5 mg/mL CD-RAP and a charged amino acid or salt thereof, preferably the salt is a chloride, phosphate, acetate or sulphate, more preferably, in addition, a buffer, a disaccharide, a bulking agent, and optionally a surfactant are rendered sufficiently stable for long-term storage and/or one or more freeze/thaw cycles. The formulation of the invention has many advantages over standard buffered formulations. In one aspect, the formulation comprises high CD-RAP protein concentrations, e.g., 30 mg/mL or more. Surprisingly, despite the high concentration of protein, the formulation has minimal aggregation and can be stored using various methods and forms, e.g., freezing, without deleterious effects that might be expected with high protein formulations.

In some less preferred embodiments, the formulations of the invention do not require excipients, such as, for example, surfactants and buffering systems, which are used in traditional formulations to stabilize proteins in solution. In addition, the formulations described herein are preferred over standard formulations because they have decreased immunogenicity due to the lack of additional agents needed for protein stabilization.

Thus, the present invention is directed to a liquid formulation, preferably a stable liquid formulation that surprisingly allows for long-term storage of CD-RAP polypeptide or biologically active analogue thereof having an amino acid sequence that shares at least 63% sequence homology with the four cysteine skeleton of CD-RAP, amino acids 12 to 107 of SEQ ID No. 1 as described herein below at a concentration of at least 5 mg/mL, preferably at least 7.5 mg/mL, more preferably at least 10 mg/mL, even more preferably at least 15 mg/mL, particularly preferred at least 20 mg/mL, more particularly preferred at least 25 mg/mL, even more particularly preferred at least 30 mg/mL and a charged amino acid or salt thereof, preferably a chloride, phosphate, acetate or sulphate. This formulation is useful, in part, because it is more convenient to use for the patient, as the CD-RAP polypeptide of this formulation is highly concentrated so as to reduce side effects like pain due to high volume injection. Furthermore, application of the formulation to a patient under low level of dynamic fluid pressure with intra-articular injection enhances chondrogenesis.

The formulation of the invention (sometimes also referred to herein as "composition of matter" or "composition") may preferably be in various physical states such as liquid, frozen, lyophilized, freeze-dried, spray-dried and reconstituted formulations, with liquid and lyophilized being preferred. Preferably, the formulation has a pH of 6.0 and more, further preferably between 5.5 and 9.0, more preferably the formulation has a pH between 6.0 and 8.0, further more preferably between 6.5 and 7.6, most preferably between 7.0 and 7.5.

"Liquid formulation" as used herein refers to a composition of matter that is found as a liquid, characterized by free movement of the constituent molecules among themselves but without the tendency to separate at room temperature. Liquid formulations include aqueous and non-aqueous liquids, with aqueous formulations being preferred. An aqueous formulation is a formulation in which the solvent is water. The dissolution of the CD-RAP polypeptide in the formulation may be homogenous or heterogeneous, with homogenous being preferred as described above.

Any suitable non-aqueous liquid may be employed provided that it provides stability to the formulation of the invention. Preferably, the non-aqueous liquid is a hydrophilic liquid. Illustrative examples of suitable non-aqueous liquids include: glycerol; dimethyl sulfoxide (DMSO); polydimethylsiloxane (PMS); ethylene glycols, such as ethylene glycol, diethylene glycol, triethylene glycol, polyethylene glycol ("PEG") 200, PEG 300, and PEG 400; and propylene glycols, such as dipropylene glycol, tripropylene glycol, polypropylene glycol ("PPG") 425 and PPG 725.

"Mixed aqueous/non-aqueous liquid formulation" as used herein refers to a liquid formulation that contains a mixture of water and an additional liquid composition.

When used herein a "formulation" is a mixture of a CD-RAP polypeptide (i.e., the active drug/substance) and further chemical substances and/or additives required for a medicinal product which is preferably in a liquid state. A formulation of the invention includes a pharmaceutical formulation. The term "pharmaceutical formulation" refers to formulations which are in such a form as to permit the biological activity of the active ingredients to be effective, and, therefore, may be administered to a subject for therapeutic use as described herein.

The preparation of the formulation includes the process in which different chemical substances, including the active drug, are combined to produce a final medicinal product such as a pharmaceutical composition. The active drug of the formulation of the invention is a CD-RAP polypeptide. The term "polypeptide" may be used herein interchangeably with the term "protein" and, as used herein, encompasses a peptide, a polypeptide, a protein, and a fusion protein. Proteins may be made by recombinant or synthetic methods.

In certain embodiments, the CD-RAP protein to be formulated is essentially pure and/or essentially homogeneous (i.e., substantially free from contaminating proteins, etc). The term "essentially pure" protein means a composition comprising at least about 80% preferably 90% by weight of the protein fraction, preferably at least about 95% by weight of the protein fraction, more preferably 97% by weight of the protein fraction or most preferably 98% by weight of the protein fraction. The term "essentially homogeneous" protein means a composition comprising at least about 99% by weight of the protein fraction, excluding the mass of various stabilizers and water in solution.

The CD-RAP polypeptide of the formulation of the invention is known in the art (see EP-B1 710 248 or EP-B1 1 146 897) and/or described herein. The CD-RAP (Cartilage derived retinoic add sensitive protein) polypeptide applied in the formulations of the invention is the CD-RAP polypeptide, also named MIA (melanoma inhibitory activity), OTOR (fibrocyte derived protein, FDP, MIA-like, MIAL) and TANGO 130 which belongs to a class of secreted proteins as described in Bosserhoff et al. (2004), Gene Expr. Patterns. 4: 473-479; Bosserhoff and Buettner (2003), Biomaterials 24: 3229-3234: Bosserhoff et al. (1997), Dev. Dyn. 208: 516-525; WO 00/12762; WO 2004/015078: EP-B1 710 248: US 2002/0103360; or EP-B1 1 146 897). The CD-RAP protein applied in the formulation of the invention is preferably a recombinant human CD-RAP protein (rh CD-RAP).

It is also preferred that the CD-RAP polypeptide of the formulation of the invention is a polypeptide comprising or having the mature sequence of CD-RAP (SEQ ID No. 1) and functional fragments or variants thereof, b) a polypeptide having at least 63%, more preferably 70%, even more preferably 80%, further preferably 90%, most preferably 95% amino acid sequence homology with the four cysteine skeleton of CD-RAP, amino acids 12 to 107 of SEQ ID No. 1, or c) a polypeptide having any of the generic sequences 1 to 3 defined herein (SEQ ID Nos. 2, 3 and 4). A variant of CD-RAP is the protein having SEQ ID NO: 4 or a mature form thereof as described in WO 2004/015078 or the protein having SEQ ID NO.14 or a mature form thereof as described in US 2002/0103360.

"Percent (%) amino acid sequence homology" with respect CD-RAP sequences identified herein is defined as the percentage of amino acid residues in a candidate sequence that are identical with the amino acid residues in the CD-RAP sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared.

Functional fragments having the same biological function as CD-RAP preferably have a length of at least 20, in particular, at least 40 and more preferably at least 50; most preferably 80 contiguous amino acids of the sequence shown in SEQ ID No. 1. Preferably, the functional fragments comprise the amino acids from position 1 to 50, 1 to 70, 1 to 80, 20 to 80, 20 to 107 of SEQ ID No 1.

```
Mature CD-RAP sequence (SEQ ID No. 1):
GPMPKLADRKLCADQECSHPISMAVALQDYMAPDCRFLTIHRGQVVYVFS

KLKGRGRLFWGGSVQGDYYGDLAARLGYFPSSIVREDQTLKPGKVDVKTD

KWDFYCQ

Generic sequence 1 (SEQ ID No. 2):
C X_4 C X_17 C X_12 V X_{11-13} W X_{7-18} F X_4 V X_21 C X Generic sequence 2 (SEQ ID No. 3)
K X C X D X E C X_11 D X_3 P D C X_12 V X_2 K L X_{7-9} W

X G S X_{5-13} G Y F P X_3 V X_18 D F X C X

Generic sequence 3 (SEQ ID No. 4):
K X C X D X_2 C X_8 A X_2 D X_3 P D C R F X_5 G X V X_5

K L X_7 W X G S V X_12 G Y F P X_22 D F X C Q
``` wherein "X" at each occurrence independently represents any amino acid and the number in lower case indicates the number of any amino acid. Preferably, "X" independently represents a naturally occurring amino acid and, in particular, A, R, N, D, C, Q, E, G, H, I, L, K, M, F, P, S, T, W, Y or V. "X" may also represent a non-standard amino acids such as lanthionine, 2-aminoisobutyric acid, dehydroalanine, ornithine, citrulline, beta alanine or norleucine. Of course, post-translational modifications commonly known in the art are also envisaged. Thus, a CD-RAP polypeptide of the invention may be post-translationally modified.

A CD-RAP protein applied in the formulation of the invention can be expressed from intact or truncated genomic DNA or cDNA or from synthetic DNAs in prokaryotic or eukaryotic host cells. Proteins can be isolated from the culture media or inclusion bodies and/or refold to form biological active compositions. See e.g. EP-B1 710 248 and Lougheed et al. (2001), Proc. Natl. Acad. Sci. U.S.A 98: 5515-5520 for exemplary protocols for recombinant protein purification of CD-RAP. Detailed description of how to test the activity (e.g. chondrogenesis) of such isolated proteins is described in Tscheudschilsuren et al. (2005), Exp. Cell Res. 1-10; or Stoll et al. (2003), Protein Sci. 12: 510-519). A bioassay for cartilage induction is described in example 2 to 5 in EP-B1 1 146 897. Further bioassays are described infra and in Example 7 and 8.

Methods of genetically engineering cells to produce polypeptides are well known in the art. See, e.g., Ausubel et al., eds. (1990), Current Protocols in Molecular Biology (Wiley, New York). Such methods include introducing nucleic acids that encode and allow expression of the polypeptide into living host cells. These host cells can be bacterial cells, fungal cells, or, preferably, animal cells grown in culture. Bacterial host cells include, but are not limited to, *Escherichia coli* cells. Examples of suitable *E. coli* strains include: HB101, DH5a, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. A few examples of animal cell lines that can be used are CHO, VERO, BHK, HeLa, Cos, MDCK, 293, 3T3, and WI38. New animal cell lines can be established using methods well known by those skilled in the art (e. g., by transformation, viral infection, and/or selection). Optionally, the polypeptide can be secreted by the host cells into the medium.

Techniques for polypeptide purification such as fractionation on an ion-exchange column, ethanol precipitation, reverse phase HPLC, chromatography on silica, chromatography on heparin SEPHAROSET, chromatography on an anion or cation exchange resin (such as a polyaspartic acid column), chromatofocusing, SDS-PAGE, and ammonium sulfate precipitation can be utilized depending on need. A CD-RAP protein applied in the formulation of the invention may be expressed and purified as described in the Examples of EP-B1 1 697 523.

In some embodiments, the concentration of a CD-RAP protein in a formulation of the invention is at least 5 mg/mL, preferably at least 7.5 mg/mL, more preferably at least 10 mg/mL, even more preferably at least 15 mg/mL, particularly preferred at least 20 mg/mL, more particularly preferred at least 25 mg/mL, even more particularly preferred at least 30 mg/mL.

In some embodiments, the concentration of CD-RAP polypeptide in a formulation of the invention is chosen from the following ranges: from about 5 mg/mL to about 10 mg/mL, from about 10 mg/mL to about 20 mg/mL, from about 15 mg/mL to about 25 mg/mL, from about 20 mg/mL to about 30 mg/mL, or from about 5 mg/mL to about 30 mg/mL.

In a preferred aspect, the CD-RAP formulation, in particular the stable aqueous formulation of the invention does not comprise liposomes and/or matrix material. Preferably, the CD-RAP formulation of the invention does not comprise liposomes and/or matrix material selected from the group of hyaluronic acid, alginate, collagen, heparin, fibrin, fibrinigen, demineralized bone, polylactic-coglycolid and/or polylactic-coglycolid derivatives or combinations thereof. More preferably, the CD-RAP formulation does not contain a lipid bilayer.

In a further preferred aspect the CD-RAP protein is not comprised at a concentration of 1-4 mg/mL including, 1.0 mg/mL, 1.5 mg/mL, 2.0 mg/mL, 2.5 mg/mL, 3.0 mg/mL, 3.5 mg/mL, 4.0 mg/mL in an arginine/$H_3PO_4$, preferably at a concentration from 350-420 mM. More preferably, the CD-RAP protein is not comprised at a concentration of 1.15 mg/mL or 3 mg/mL in a 350 mM or 420 mM arginine/$H_3PO_4$ pH 7.5.

When used herein, the term "about" is understood to mean that there can be variation in the concentration of a CD-RAP protein of the described formulation that can be to 5%, 10%, 15% or up to and including 20% of the given value. For example, if a formulation has about 5 mg/mL of CD-RAP polypeptide, this is understood to mean that a formulation can have between 3 to 7 mg/mL, more preferably between 4 to 6 mg/mL. Thus, as used herein, a concentration interval which is defined as "X to Y" equates with an interval which is defined as "between X and Y". Both time intervals specifically include the upper limit and also the lower limit. This means that for example an interval "5 mg/mL to 10 mg/mL" or between "5 mg/mL to 10 mg/mL" includes a concentration of 5, 6, 7, 8, 9, and/or 10 mg/mL.

A "stable" formulation is one in which the protein therein essentially retains its physical stability and/or chemical stability and/or biological activity upon storage and/or shows substantially no signs of aggregation, precipitation and/or denaturation compared to a control sample, preferably upon visual examination of color and/or clarity, or as measured by UV light scattering or by size exclusion chromatography. Various further analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example.

Preferably, the term "stable" with respect to the formulation of the invention is understood to mean that the CD-RAP polypeptide of the formulation does not lose more than 15%, or more preferably 10%, or even more preferably 5%, and most preferably 3% of its biological activity during storage relative to activity of the CD-RAP polypeptide at the beginning of storage and/or during or after freeze-thawing. CD-RAP biological activity can, for example, be determined by the bioassay for cartilage induction is described in example 2 to 5 in EP-B1 1 146 897. Other bioassays are the invasion assay described in Stoll et al., (2006), Biol. Chem., Vol. 387, pp. 1601-1606 or in Example 7 and 8.

"During storage," as used herein, means a formulation that once prepared, is not immediately used; rather, following its preparation, it is packaged for storage, either in a liquid form, in a frozen state, or in a dried form for later reconstitution into a liquid form or other form.

"Repeated freeze-thaw cycles" includes that the formulation of the invention is subjected to one or more freeze-thaw cycles, e.g., one, two, three, four, five or more freeze-thaw cycles. However, as is described herein and shown in the Examples, the formulation of the invention remains stable under repeated free-thaw cycles. Accordingly, the CD-RAP polypeptide is preferably stable under repeated (one, two, three, preferably four, five or more) freeze-thaw cycles, preferably the freeze-thaw cycle is as follows: 5° C. to −25° C., cooling and heating rate 1.0° C./min with an isothermal step of 15 min between each cycle. Without being bound by theory, the freeze-thaw cycle which is preferably applied in the context of the invention simulates freezing stress which may occur during freezing of large amounts of dissolved protein. Accordingly, since the formulation of the invention turned out to be capable of keeping CD-RAP stably in solution during that freeze-thaw cycle, the formulation of the invention is superior and has advantageous properties.

Aggregates may be formed during storage, for example, because of exposure to elevated temperatures. By "elevated temperature" is meant any temperature above the temperature at which the formulation of the invention comprising a CD-RAP polypeptide is normally stored. The normal storage temperature is between about 4° C. and 10° C., preferably between about 4° C. and 8° C., more preferably between about 4° C. and 6° C., even more preferably at a temperature of about 4° C. Further causes for the formation of aggregates may be the pH of the formulation, the ionic strength of the formulation, the presence of certain surfactants (e.g., polysorbate-20 and polysorbate-80), emulsifying agents and/or because a polypeptide has an inherent tendency to form such aggregates. Without being bound by theory, it is assumed that aggregate formation of CD-RAP polypeptides could be caused by one or more of the aforementioned causes and may lead to a loss of activity.

Accordingly, it is envisaged that a CD-RAP polypeptide is preferably stable insofar that it does not substantially form aggregates (for example, because of one or more of the aforementioned causes) during storage and/or during or after freeze-thawing. Accordingly, it is preferably envisaged that not more than 10% of a CD-RAP polypeptide, more preferably not more than 8%, even more preferably not more than 5%, even further preferably not more than 3%, particularly preferably not more than 1% relative to the amount of the CD-RAP polypeptide at the beginning of storage forms aggregates.

In the alternative, it is envisaged that a CD-RAP polypeptide is preferably stable insofar that it does not form dimers or oligomers. Put it differently, the stability of a CD-RAP protein can be determined according to the percentage of monomer protein in the solution, with a low percentage of degraded (e.g., fragmented) and/or aggregated protein. For example, a formulation of the invention comprising a CD-RAP protein may include at least 90%, more preferably at least 92%, even more preferably at least 95%, further even more preferably at least 97%, particularly preferably at least 98%, most preferably 99% monomer CD-RAP protein.

By "aggregate" is meant a physical interaction between protein molecules that results in the formation of covalent or non-covalent dimers or oligomers (i.e. high molecular weight entities) which may remain soluble, or form insoluble aggregates that precipitate out of solution. An "aggregate" also includes degraded and/or fragmented CD-RAP protein. The level of protein aggregation in a formulation may be measured before, at substantially the same time as, or after, the addition of a charged amino acid as described herein to the formulation. In certain embodiments, the level of aggregation is measured at least once between about 1 day and about 12 weeks after the addition of a charged amino acid as described herein to the formulation. In other embodiments, the level of aggregation is measured at least once between about 1 month and 36 months after the addition of a charged amino acid as described herein to the formulation.

As mentioned herein above, a number of different analytical methods can be used to detect the presence and levels of aggregates in a formulation comprising a protein. These include, but are not limited to, for example, native polyacrylamide gel electrophoresis (PAGE), sodium dodecyl sulfate-polyacrylamide gel electrophoresis (SDS-PAGE), capillary gel electrophoresis (CGE), size exclusion chromatography (SEC), analytical ultracentrifugation (AUC), field flow fractionation (FFF), light scattering detection, sedimentation velocity, UV spectroscopy, differential scanning calorimietry, turbidimetry, nephelometry, microscopy, size exclusion chromatography-high performance liquid chromatography (SEC-HPLC), reverse phase-high performance liquid chromatography (RP-HPLC), electrospray ionization tandem mass spectroscopy (ESI-MS), and tandem RP-HPLC/ESI-MS, flow field-flow fractionation technique and static and/or dynamic light scattering. These methods may be used either alone, or in combination. Preferably, the analytical methods to detect the presence and levels of aggregates in a formulation comprising a protein, preferably CD-RAP, are size exclusion chromatography-high performance liquid chromatography (SEC-HPLC) and flow field-flow fractionation technique static and/or dynamic light scattering.

A common problem with a formulation comprising a protein is the irreversible accumulation of aggregates with time, thermal, or shear stress. Typically, when aggregates precipitate they form large particles that are easy to detect. Smaller, non-covalent soluble aggregates, however, which are often precursors to precipitating large particles, are more difficult to detect and quantitate. Thus, methods to detect and quantitate protein aggregation in a protein formulation need to be based on the kind of aggregate being assessed.

Among the above methods, the suggested methods to determine the presence and/or amounts of soluble, covalent aggregates in a protein formulation are: SEC/light scattering, SDS-PAGE, CGE, RP-HPLC/ESI-MS, FFF and AUC: The suggested methods to determine the presence and/or amounts of soluble, non-covalent aggregates in a protein formulation are: SEC, PAGE, SDS-PAGE, CGE, FFF, AUC, and dynamic light scattering. The suggested methods to determine the presence and/or amounts of insoluble, non-covalent aggregates in a protein formulation are: UV spectroscopy, turbidimetry, nephelometry, microscopy, AUC, and dynamic light scattering.

Given the above, it is another embodiment of the invention to provide a method for accelerated stability testing of the stability a CD-RAP polypeptide in a formulation of the invention comprising the steps of testing the activity of the polypeptide formulated according to the invention prior to storage, i.e., time zero, storing the composition at about between 37° C. and 42° C., preferably at about 37° C. for at least one month and measuring the stability of the polypeptide, and comparing the stability from time zero to the one month time point. This information is helpful for early elimination of batches or lots that appear to have good stability initially, yet do not store well for longer periods.

Moreover, the formulation of the invention preferably provides improved long-term storage such that the CD-RAP protein is stable over the course of storage either in liquid or frozen states, preferably in liquid form. As used herein, the phrase "long-term" storage is understood to mean that the formulation can be stored for at least one month, two or three months or more, for six months or more, and preferably for one year or more. Long term storage is also understood to mean that the pharmaceutical composition is stored either as a liquid at 2-8 C or is frozen, e.g., at −20° C. or colder, thereby the formulation does preferably not lose its biological activity to the extent as described herein and/or does not form aggregates to the extent as described herein and/or comprises monomers to the extent as described herein. Tests for these properties are described herein elsewhere. It is also contemplated and demonstrated in the Examples that the formulation can be frozen and thawed more than once.

In one aspect of the invention, the CD-RAP protein in the formulations is stable in a liquid form for at least 1 month, 2 month, 3 months; at least 4 months, at least 5 months; at least 6 months; at least 12 months. Ranges intermediate to the above recited time periods are also intended to be part of this invention, e.g., 9 months, and so forth. In addition, ranges of values using a combination of any of the above recited values as upper and/or lower limits are intended to be included. Preferably, the formulation is stable at room temperature (about 20° C.) or at 30° C. for at least 1 month and/or stable at about 2-8° C. for at least 1, 2, 3, 4, 5, 6, 7, 8, 9, 10, 11 or 12 months, or more preferably stable at about 2-8° C. for at least 2 years. Furthermore, the formulation is preferably stable following freezing (to, e.g., −80° C.) and thawing of the formulation, herein also referred to as a "freeze/thaw cycle."

Unexpectedly, the present inventors aiming at stabilizing a CD-RAP protein at a high concentration, have found that an amino acid which has a net charge at a pH between about 6 and 8 allows the preparation of highly concentrated CD-RAP formulations and acts to reduce aggregation of CD-RAP polypeptides in such a formulation for long periods, thereby enabling a stable formulation as described herein.

Accordingly, in a preferred aspect, the charged amino acid comprised by the stable formulation of the invention has a net charge at a pH between about 6 and 8.

The term "net charge" is meant that positive and negative charges on the surface of the amino acid or protein which depend on the nature of the amino acid or the amino acids of the protein is not zero. The net charge depends on the number and identities of the charged amino acids, and on pH as well as on the position of the amino acid within the primary sequence of a polypeptide. At a specific pH the positive and negative charges will be balanced and the net charge will be zero. This pH is called the isoelectric point where the protein has its lowest solubility.

More preferably, the amino acid or charged amino acid is selected from the group consisting of glycine, arginine, lysine, histidine, aspartic acid, glutamic acid and salts thereof. Histidine, glutamate, arginine or a salt thereof is particularly preferred. In some embodiments, combinations of the aforementioned amino acids or salts thereof are applied in the formulation of the invention.

In further embodiments, the amino acid is an analogue of arginine, lysine or histidine that retains the ability to enhance solubility of CD-RAP preferably at pH 6.0 or greater. Such analogues include, without limitation, dipeptides and tripeptides that contain arginine, lysine or histidine.

In further preferred embodiments the amino acid salt is arginine chloride (preferably in a solution between pH 6.0 to 8.0, more preferably between pH 6.5 and 7.5, most preferably at pH 6.0 or 7.4), arginine phosphate (preferably in a solution between pH 6.0 to 8.0, more preferably between pH 6.5 and 7.5, most preferably at pH 6.0 or 7.4), histidine phosphate (preferably in a solution between pH 6.0 to 8.0, more preferably between pH 6.5 and 7.5, most preferably at pH 6.0 or 7.4), histidine chloride (preferably in a solution between pH 6.0 to 8.0, more preferably between pH 6.5 and 7.5, most preferably at pH 6.0 or 7.4), potassium and sodium glutamate (preferably in a solution between pH 6.0 to 8.0, more preferably between pH 6.5 and 7.5, most preferably at pH 6.0 or pH7.4). The amino acids and salts thereof applied in the invention are well known in the art and are manufactured by known methods and available from commercial suppliers.

The concentration of the charged amino acid, salt thereof or any specified amino acid such as glycine, arginine, lysine, histidine, aspartic acid, glutamic acid and salts thereof in the formulation is preferably between about 0.5% (w/v) to about 8% (w/v), 1% (w/v) to about 8% (w/v), 1% (w/v) to about 5% (w/v), 1.5% (w/v) to about 5% (w/v), 2. % (w/v) to about 5% (w/v), 0.5% (w/v) to about 3% (w/v), more preferably about 1.0% (w/v) to about 3% (w/v), even more preferably about 1.5% (w/v) to about 3% (w/v), even further preferably 2.0% (w/v) to about 3% (w/v), and particularly preferably at about 2.5% (w/v). The charged amino acids are available from commercial suppliers.

The formulation of the invention is prepared by combining, in addition to a CD-RAP polypeptide as described herein, an amino acid which has a net charge at a pH between about 6 and 8 e.g. in an aqueous solution.

Further, a buffer, a tonicity modifier and/or a stabilizer and, optionally, an additional excipient can be added as needed. Persons having ordinary skill in the art will understand that the combining of the various components to be included in the formulation can be done in any appropriate order. For example, the buffer can be added first, middle or last and the tonicity modifier can also be added first, middle or last. It is also to be understood by one of ordinary skill in the art that some of these chemicals can be incompatible in certain combinations, and accordingly, are easily substituted with different chemicals that have similar properties but are compatible in the relevant mixture.

In a preferred embodiment of the invention the amino acid comprised in the formulation of the invention and any one of the further ingredients such as a buffer, tonicity modifier, stabilizer, excipient that may be comprised in the formulation is chosen such that it provides stability to the CD-RAP protein over repeated freeze/thaw cycles (preferably over 5 freeze/thaw cycles (5° C. to −25° C., cooling and heating rate 1.0° C./min with an isothermal step of 15 min between each cycle).

In a preferred aspect of the invention the formulation comprises a buffer.

The term "buffer" as used herein, includes those agents that maintain pH in a desired range. Buffer is an aqueous solution consisting of a mixture of a weak acid and its conjugate base or a weak base and its conjugated acid. It has the property that the pH of the solution changes very little when a small amount of a strong acid or base is added. Buffer solutions are used as a means of keeping pH at a nearly constant value in a wide variety of chemical applications. Buffer solutions are used to maintain a certain level on the pH scale. In general, a buffer when applied in the formulation of the invention preferably stabilizes a CD-RAP protein.

"Amino acid buffers" when used herein include, for example, the amino acid base e.g. arginine and its conjugated salt. Examples of amino acid buffers are arginine/arginine chloride, arginine/arginine phosphate histidine/histidine chloride, histidine/histidine phosphate/glutamic acid/sodium or potassium glutamate. These examples are preferably applied in the invention.

The preferred pH of a formulation as described herein may be chosen from the following ranges: from about 4 to about 10, from about 5 to about 9, preferably, from about 6 to about 8. Accordingly, a buffer that can maintain a solution at pH 6.0 to 8.0 is preferably used. The term "about" when used in the context of pH value/range preferably means a numeric value having a range of +/−25% around the cited value. When the pH of the pharmaceutical composition is set at or near physiological levels, comfort of the patient upon administration is maximized.

Generally, the nature of a buffer and/or the amino acid and its concentration is such that the osmolality of the formulation is between 280-320 mosmol/kg. In particular, it is preferred that the pH be within a range of pH about 5.8 to 8.4, with about 6.2 to 7.4 being preferred, more preferably the pH is between pH 5.8 to 8.4, most preferably between 6.2 to 7.4, however, it is to be understood that the pH can be adjusted as necessary to maximize stability and solubility of the polypeptide in a particular formulation and as such, a pH outside of physiological ranges, yet preferably tolerable to the patient, is within the scope of the invention.

Non-limiting examples of buffers that may be used in a formulation described herein include, histidine, succinate, gluconate, citrate, tris (trometamol), Bis-Tris, MOPS, ACES, TES, HEPES, EPPS, ethylenediamine, phosphoric acid, maleic acid/phosphate, citrate, 2-morpholinoethanesulfonic acid (MES), sodium phosphate, sodium acetate and diethanolamine.

Preferred buffers are phosphate buffers, Tris buffers, amino acid buffers such as but not limited to arginine, histidine and glutamate buffer. More preferably, the following buffers are applied in the formulation of the invention: arginine phosphate (preferably between pH 6.0 to 8.0, more preferably between pH 6.5 and 7.5, most preferably at pH 6.0 or 7.4), histidine phosphate (preferably between pH 6.0 to 8.0, more preferably between pH 6.5 and 7.5, most preferably at pH 6.0 or 7.4), histidine chloride (preferably between pH 6.0 to 8.0, more preferably between pH 6.5 and 7.5, most preferably at pH 6.0 or 7.4). The buffers applied in the invention are well known in the art and are manufactured by known methods and available from commercial suppliers.

The concentration of an amino acid, salt thereof, glycine, arginine, lysine, histidine, aspartic acid, glutamic acid and salts thereof, a buffer, such as but not limited to Tris buffer, histidine buffer, arginine phosphate buffer and phosphate buffer in the compositions of the invention may be chosen from the following ranges: from about 1 to about 500 mM, from about 1 to about 450 mM, from about 1 to about 400 mM, from about 1 to about 350 mM, from about 1 to about 300 mM, from about 1 to about 250 mM, from about 1 to about 200 mM, from about 1 to about 150 mM, from about 1 to about 100 mM, from about 1 to about 50 mM, from about 1 to about 40 mM, from about 1 to about 30 mM, from about 1 to about 20 mM, from about 1 to about 10 mM, from about 10 to about 500 mM, 10 to about 450 mM, 10 to about 400 mM, 10 to about 350 mM, 10 to about 300 mM, 10 to about 250 mM, 10 to about 200 mM, 10 to about 150 mM, from about 30 to about 500 mM, 30 to about 450 mM, 30 to about 400 mM, 30 to about 350 mM, 30 to about 300 mM, 30 to about 250 mM, 30 to about 200 mM, or 30 to about 150 mM.

For a Tris buffer the most preferred concentration is 30 to 100 mM, for a histidine buffer the preferred concentration is 45 to 60 mM or 250 to 350 mM, most preferably 50 mM to 300 mM, for a phosphate buffer the preferred concentration is 45 to 60 mM, for an arginine buffer the preferred concentration is 250 to 380 mM and for a glutamate buffer the preferred concentration is 250 to 360 mM, most preferably 280 to 360 mM.

In a preferred aspect of the invention, the formulation comprises a tonicity modifier. As used herein, the term "tonicity modifier" is intended to mean a compound or compounds that can be used to adjust the tonicity of a liquid formulation. Suitable tonicity modifiers include glycerin, lactose, mannitol, dextrose, sodium chloride, magnesium sulfate, magnesium chloride, potassium chloride, sodium sulfate, sorbitol, trehalose, sucrose, raffinose, maltose and others known to those or ordinary skill in the art. In one embodiment, the tonicity of the liquid formulation approximates that of the tonicity of blood or plasma. A tonicity modifier contributes to the osmolality of the composition. The osmolality of human serum is about 250-350 mOsM/kg. To maintain protein stability and minimize patient discomfort, it is generally preferable that the formulation be isotonic, i.e., having approximately equal osmolality, with human serum or synovial fluid. Accordingly, the osmolality of the composition is preferably from 180 to 420 mOsM/kg, more preferably from 280 to 320 mOsM/kg. Within this range is the most desired osmolality, i.e., isotonicity. The term "isotonic" means that the formulation of interest has essentially the same osmotic pressure as human blood. Isotonic formulations will generally have an osmotic pressure from about 270-328 mOsM. Slightly hypotonic osmotic pressure is 250-269 and slightly hypertonic osmotic pressure is 328-350 mOsm. Osmotic pressure can be measured, for example, using a vapor pressure or ice-freezing type osmometer.

However, one of skill in the art will understand that the osmolality of the composition may be higher or lower as specific conditions require. A variety of tonicity modifiers are known in the art (see, e.g., paragraph [0047] of U.S. Patent Application 2003/0180287). Other components of the formulation, including, but not limited to, salts (e.g., sodium chloride, potassium chloride and sodium citrate), buffers, disaccharides (e.g., sucrose, glucose and mannitol), bulking agents, and surfactants, may also contribute to the osmolality of the composition. The concentration of the tonicity modifier in the formulation is preferably between about 1 mM to 1000 mM, more preferably about 10 mM to about 200 mM. A preferred tonicity modifier applied in the formulation of the invention is potassium chloride or sodium chloride, preferably at a concentration of less than 150 mM, less than 100 mM, less than 80 mM, less than 50 mM, at a concentration of 10 to 50 mM, 40 to 90 mM, 40 to 120 mM, 50 to 120 mM, 50 to 150 mM, 80 to 150 mM, 80 to 120 mM, 40 to 45 mM, 80 to 90 mM, 100 to 150 mM, 100 to 120 mM, 42.5 mM, 89.5 mM, 116.5 mM or 150 mM.

In some embodiments, the formulation further comprises sodium chloride (NaCl). In particular embodiments, the formulation comprises 1-200 mM, or less than 50 mM, less than 40 mM, less than 35 mM, less than 30 mM, less than 25 mM, less than 20 mM, less than 15 mM, less than 10 mM, or less than 5 mM NaCl. Under certain conditions, NaCl may cause a difficulty during lyophilization or lead to the appearance of opalescence in the reconstituted lyophilate. Accordingly, in a less preferred embodiment, the formulation does not comprise NaCl.

In addition to the CD-RAP protein, a formulation as described herein may also contain other substances. These substances include, but are not limited to, stabilizing agents (stabilizers).

Accordingly, in a preferred aspect, the formulation comprises a stabilizer. The term "stabilizing agent" refers to an agent that improves or otherwise enhances stability of the formulation, in particular of the CD-RAP protein. A stabilizing agent may be a disaccharide, a sugar alcohol, a metal chelator or a combination of metal chelators, a radical scavenger or combinations thereof.

Preferably, the disaccharide when used as stabilizing agent may be a non-reducing sugar, e.g., sucrose, trehalose or mannose. In certain embodiments, the concentration of disaccharide in the composition is chosen from the following ranges: from 0.5 to 5%, from 0.5 to 4%, from 0.5 to 3%, from 0.5 to 2.5%, from 0.5 to 2%, from 0.5 to 1.5%, from 0.5 to 1%, from 1 to 1.5%, from 1.5 to 2%, from 2 to 2.5%, from 2.5 to 3%, from 3 to 4%, from 4 to 5% or more than 5% (w/v). In particular embodiments, the concentration of disaccharide in the composition is about 0.5 to 5%, for example about 0.5 to 2.0% (w/v). A preferred stabilizer applied in the formulation of the invention is sucrose, preferably at 5.0% or mannitol, preferably at 5.0% (w/v).

The stabilizing agent may also be a sugar alcohol such as glycol, glycerol, erythritol, threitol, arabitol, xylitol, ribitol, mannitol, sorbitol, dulcitol, iditol, isomalt, maltitol, lactitol or polyglycitol.

Another stabilizer may be a metal chelator or a combination of metal chelators. In specific embodiments, the metal chelators are DTPA, EGTA and DEF. In some embodiments, the concentration of DTPA or EGTA in the protein formulation is from about 1 µM to about 10 mM, from about 1 µM to about 5 mM, from about 10 µM to about 10 mM, 50 µM to about 5 mM, or from about 75 µM to about 2.5 mM. In some embodiments, the concentration of DEF in the protein formulation is from about 1 µM to about 10 mM, from about 1 µM to about 5 mM, from about 10 µM to about 1 mM, or from about 20 µM to about 250 µM.

The stabilizer can also be a free radical scavenger, especially a scavenger of oxygen radicals. In specific embodiments, the free radical scavenger is mannitol or histidine. In some embodiments, the concentration of mannitol in the protein formulation is from about 0.01% to about 5%, from about 0.1% to about 5%, from about 0.5% to about 5%, or from about 1% to about 5%.

In other embodiments, the agent that reduces aggregation of the protein of the formulation is a combination of a metal chelator and a free radical scavenger. In some embodiments, the agent that reduces aggregation of a protein or proteins in a formulation is citrate. In certain embodiments, the concentration of citrate in the protein formulation is from about 0.5 mM to about 50 mM, from about 0.5 mM to about 25 mM, from about 1 mM to about 35 mM, from about 5 mM to about 25 mM, or from about 5 mM to about 10 mM.

In a preferred embodiment, a formulation described herein comprises an excipient. Preferably the excipient is selected from the group consisting of a cryoprotectant, a lyoprotectant, a surfactant, a bulking agent, an anti-oxidant, and combinations thereof.

Excipients, also referred to as chemical additives, co-solutes, or co-solvents, that preferably stabilize the CD-RAP polypeptide while in solution (also in dried or frozen forms) can also be added to a formulation of the invention. Preferably, excipients contribute to the stability of the CD-RAP protein, but it is to be understood that excipients may otherwise contribute to the physical, chemical, and biological properties of the formulation. Excipients are well known in the art and are manufactured by known methods and available from commercial suppliers.

Examples of excipients include but are not limited to sugars/polyols such as: sucrose, lactose, glycerol, xylitol, sorbitol, mannitol, maltose, inositol, trehalose, glucose; polymers such as: serum albumin (bovine serum albumin (BSA), human SA or recombinant HA), dextran, PVA, hydroxypropyl methylcellulose (HPMC), polyethyleneimine, gelatin, polyvinylpyrrolidone (PVP), hydroxyethylcellulose (HEC), hydroxyethylstarch (HES); non-aqueous solvents such as: polyhydric alcohols, (e. g., PEG, ethylene glycol and glycerol) dimethysulfoxide (DMSO) and dimethylformamide (DMF); amino acids such as: proline, L-serine, sodium glutamic acid, alanine, glycine, lysine hydrochloride, sarcosine and gamma-aminobutyric acid; surfactants such as: Tween-80, Tween-20, SDS, polysorbate, polyoxyethylene copolymer; and miscellaneous excipients such as: potassium phosphate, sodium acetate, ammonium sulfate, magnesium sulfate, sodium sulfate, trimethylamine N-oxide, betaine, metal ions (e. g., zinc, copper, calcium, manganese, and magnesium), CHAPS, monolaurate, 2-O-beta-mannoglycerate or any combination of the above. In certain embodiments, the concentration of surfactant in the formulation is from 0.001 to 5.0%, from 0.001 to 2.5%, from 0.001 to 1%, from 0.001 to 0.5%, from 0.001 to 0.2%, from 0.001 to 0.1%, from 0.001 to 0.05%, from 0.001 to 0.01%, or from 0.001 to 0.005% per weight.

"Cryoprotectants" include substances that provide stability to the frozen protein during production, freezing, storage, handling, distribution, reconstitution, or use. In a particular aspect, "cryoprotectants" include substances that protect the protein from stresses induced by the freezing process. Cryoprotectants may have lyoprotectant effects. Non-limiting examples of cryoprotectants include sugars, such as sucrose, glucose, trehalose, mannitol, mannose, and lactose; polymers, such as dextran, hydroxyethyl starch and polyethylene glycol; surfactants, such as polysorbates (e.g., PS-20 or PS-80); and amino acids, such as glycine, arginine, leucine, and serine. A cryoprotectant exhibiting low toxicity in biological systems is generally used. The cryoprotectant, if included in the formulation, is added to a final concentration of between about 1% and about 10% (w/v), preferably to a final concentration of 0.5 to 8% (w/v), 0.5 to 6% (w/v), 0.5 to 8% (w/v), 0.5 to 5% (w/v), 1 to 8% (w/v), 1 to 6% (w/v), 1 to 8% (w/v), 1 to 5% (w/v), 1.5 to 8% (w/v), 1.5 to 6% (w/v), 1.5 to 8% (w/v), 1.5 to 5% (w/v), 2 to 8% (w/v), 2 to 6% (w/v), 2 to 8% (w/v), 2 to 5.5% (w/v).

A disaccharide as described herein may act as a lyoprotectant or cryoprotectant. "Lyoprotectants" include substances that prevent or reduce chemical or physical instability of a protein upon lyophilization and subsequent storage. In one aspect, the lyoprotectant prevents or reduces chemical or physical instabilities in the protein as water is removed from the composition during the drying process. In a further aspect, the lyoprotectant stabilize the protein by helping maintain the proper conformation of the protein through hydrogen bonding.

Accordingly, in one aspect, a disaccharide as described herein may serve to stabilize the CD-RAP protein during freezing. As protection during freezing may depend upon the absolute concentration of the disaccharide (Carpenter et al., Pharm. Res. (1997), 14:969-975, concentrations greater than 5% may be necessary to maximize stability.

In one aspect, the disaccharide stabilizes the CD-RAP protein during drying. Protection during drying may depend upon the final mass ratio between the final mass ratio between the disaccharide and the protein. Carpenter et al., Pharmaceutical Research 14:969-975 (1997). Accordingly, in some embodiments, the concentration of disaccharide is selected to achieve the desired mass ratio of disaccharide to protein, typically at least 1:1. In some embodiments, stability is optimized at a disaccharide:protein mass ratio of about 5:1. In other embodiments, the disaccharide:protein mass ratio is 10:1, 20:1, 30:1, 40:1, 50:1, 100:1, 200:1, 300:1, 400:1, 500:1, 600:1, 700:1, 800:1, 900:1, 1000:1, or higher than 1000:1.

In one embodiment, a lyoprotectant is added to a formulation described herein. The term "lyoprotectant" as used herein, includes agents that provide stability to the protein during the freeze-drying or dehydration process (primary and secondary freeze-drying cycles), by providing an amorphous glassy matrix and by binding with the protein through hydrogen bonding, replacing the water molecules that are removed during the drying process. This helps to maintain the protein conformation, minimize protein degradation during the lyophilization cycle, and improve the long-term product stability. The lyoprotectant is added to the pre-lyophilized formulation in a "lyoprotecting amount" which means that, following lyophilization of the CD-RAP protein in the presence of the lyoprotecting amount of the lyoprotectant, the protein essentially retains its physical and chemical stability and integrity upon lyophilization and storage.

Non-limiting examples of lyoprotectants include sugars, such as sucrose or trehalose; an amino acid, such as monosodium glutamate, glycine or histidine; a methylamine, such as betaine; a lyotropic salt, such as magnesium sulfate; a polyol, such as trihydric or higher sugar alcohols, e.g., arabitol, xylitol, sorbitol, and mannitol; polyethylene glycol; pluronics; and combinations thereof. The amount of lyoprotectant added to a formulation is generally an amount that does not lead to an unacceptable amount of degradation/aggregation of the protein when the protein formulation is lyophilized. Where the lyoprotectant is a sugar (such as sucrose or trehalose) and the protein is an antibody, non-limiting examples of lyoprotectant concentrations in the protein formulation are from about 10 mM to about 400 mM, and preferably from about 30 mM to about 300 mM, and most preferably from about 50 mM to about 100 mM. In certain embodiments, a surfactant may be included in the formulation.

Another preferred excipient is a surfactant. The term "surfactants" generally includes those agents that protect the CD-RAP protein from air/solution interface-induced stresses and solution/surface induced-stresses. For example surfactants may protect the protein from aggregation.

Examples of surfactants include, without limitation, nonionic surfactants, such as polysorbates (e.g., polysorbate 80 or polysorbate 20); poloxamers (e.g., poloxamer 188); Triton, sodium dodecyl sulfate (SDS); sodium laurel sulfate; sodium octyl glycoside; lauryl-sulfobetaine, myristyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, lauroamidopropyl-betaine, cocamidopropyl-betaine, linoleamidopropyl-betaine, myristamidopropyl-betaine, palmidopropyl-betaine, isostearamidopropyl-betaine (e.g., lauroamidopropyl), myristarnidopropyl-, palmidopropyl-, or isostearamidopropyl-dimethylamine; sodium methyl cocoyl-, or disodium methyl ofeyl-taurate; and the Monaquat series (Mona Industries, Inc., Paterson, N.J.), polyethyl glycol, polypropyl glycol, and copolymers of ethylene and propylene glycol (e.g., pluronics, PF68). The amount of surfactant added is such that it maintains aggregation of the reconstituted protein at an acceptable level as assayed using, e.g., SEC-HPLC to determine the percentage of high molecular weight (HMVV) species or low molecular weight (LMVV) species, and minimizes the formation of particulates after reconstitution of a lyophilate of a protein formulation described herein. For example, the surfactant can be present in a formulation (liquid, or prior to reconstitution of a lyophilate) in an amount from about 0.001 to about 0.5%, e.g., from about 0.05 to about 0.3%. A preferred surfactant applied in the formulation of the invention is polysorbate 20 or 80.

A further preferred excipient may by a bulking agent. Namely, in an aspect of the invention, it is contemplated that the formulation of the invention is prepared in a bulk formulation and as such, the components of the pharmaceutical composition are adjusted so that it is higher than would be required for administration and diluted appropriately prior to administration.

The term "bulking agent" as used herein, includes agents that provide the structure of the freeze-dried product without interacting directly with the pharmaceutical product. In addition to providing a pharmaceutically elegant cake, bulking agents may also impart useful qualities in regard to modifying the collapse temperature, providing freeze-thaw protection, and enhancing the protein stability over long-term storage. Non-limiting examples of bulking agents include mannitol, glycine, lactose, and sucrose. Bulking agents may be crystalline (such as glycine, mannitol, or sodium chloride) or amorphous (such as dextran, hydroxyethyl starch) and are generally used in protein formulations in an amount from 0.5% to 10%.

Preferably, the bulking agent applied in the formulation of the invention promotes the formation of a cake that is aesthetically acceptable, uniform, or mechanically strong. Bulking agents also preferably promote the formation of an open pore structure and the ease and speed of reconstitution. Bulking agents also preferably reduce or prevent cake collapse, eutectic melting, or retention of residual moisture. In another aspect, bulking agents preferably help protect the CD-RAP protein against stresses (e.g., physical and chemical stresses) and help maintain protein activity.

In certain embodiments, the concentration of bulking agent in the composition is chosen from the following ranges: from 1 to 10%, from 1 to 8%, from 1 to 5%, from 2 to 8%, from 2 to 6%, from 2.5 to 6%, from 0.5 to 1%, from 1 to 1.5%, from 1.5 to 2%, from 2 to 2.5%, from 2.5 to 3%, from 3 to 3.5%, from 3.5 to 4%, from 4 to 4.5%, from 4.5 to 5%, more than 5%, from 0.5 to 5%, from 0.5 to 4%, from 0.5 to 3%, from 0.5 to 2.5%, from 0.5 to 2%, from 0.5 to 1.5%, or from 0.5 to 1%. In certain embodiments, the concentration of bulking agent in the composition is 0.5 to 5%, for example 0.5 to 3%, even more precisely 1.8 to 2%.

Another preferred excipient may be an antioxidant. As used herein, an "antioxidant" is a molecule capable of slowing or preventing the oxidation of other molecules. Oxidation is a chemical reaction that transfers electrons from a substance to an oxidizing agent. For use in the methods of the invention, physiologically acceptable antioxidants are of interest. Such antioxidants include, without limitation, reducing agents, ascorbic acid (vitamin C), lipoic acid, melatonin, uric acid, carotenes, retinols, tocopherols and tocotrienols, e.g. α-tocopherol (vitamin E), ubiquinone (coenzyme Q), and the like.

In some embodiments, the formulation may optionally contain a preservative. A "preservative" is a compound which can be added to the formulations herein to reduce bacterial activity. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

The appended Examples (see Examples 3 and 4) demonstrate (see also FIGS. 6, 7, 10 and 11) that freeze thaw cycles in the tested formulations (except for CD-RAP in 50 mM potassium phosphate/5% Sucrose and 150 mM glycine pH 6.0) had no effect on protein stability. In the latter case a significant decrease in CD-RAP concentration after the third freeze/thaw cycle can be seen. However, in all other formulations the solution was clear after every freezing cycle. In combination with the results from the quantification of rhCD-RAP by UV/Vis this solves the problem of the present invention and results into suitable conditions for rhCD-RAP in high concentrations.

Accordingly, in more preferred embodiments a formulation of the invention is a liquid, preferably aqueous, formulation which comprises at least 5, 10, 15, 20, 25 or 30 mg/mL CD-RAP and a buffer selected from the group consisting of potassium or sodium phosphate, TRIS, histidine, arginine and glutamate buffer and an amino acid selected from the group consisting of aspartate, glutamate (preferably glutamate phosphate), arginine (preferably arginine phosphate or arginine chloride), histidine (preferably histidine chloride or histidine phosphate), lysine and glycine.

Glutamate, aspartate, arginine, histidine, lysine and glycine are preferably present in the formulation in an amount of 2.5% (w/v). Preferably, the buffer and the amino acid are chosen so that they provide stability to the CD-RAP protein over 5 freeze/thaw cycles (5° C. to −25° C., cooling and heating rate 1.0° C./min with an isothermal step of 15 min between each cycle).

Accordingly, in particular preferred embodiments a formulation of the invention is a liquid, preferably aqueous, formulation which comprises at least 30 mg/mL CD-RAP and 50 mM TRIS chloride and 2.5% glutamate; 50 mM histidine and 2.5% (w/v) glycine, 2.5% (w/v), glutamate (w/v) or 2.5% lysine (w/v); 300 mM histidine chloride pH 6.0; 50, 100, 200 or 300 mM histidine phosphate pH 6.0; 350 mM arginine chloride pH 6.0; 350 mM arginine phosphate pH 6.0; 350 mM arginine phosphate pH 7.4; or 300 mM potassium glutamate pH 6.0. These formulations may optionally comprise a stabiliser, tonicity modifier and/or excipient as described herein.

It is to be understood that certain components of the composition may be interchanged with alternatives known in the art. However, one skilled in the art will also understand that inclusion of certain components will preclude the use of other components, concentrations, or methods of preparing the formulation, for reasons that include, but are not limited to, chemical compatibility, pH, tonicity, and stability.

As mentioned herein, this application generally relates to the discovery that adding a charged amino acid to a formulation can reduce aggregation of CD-RAP protein at high concentrations in a formulation. Regardless of what causes a CD-RAP protein at a high concentration in a formulation to aggregate, the addition of a charged amino acid or a combination of the charged amino acids as described herein reduces aggregation of the CD-RAP protein in the formulation. In certain embodiments, addition of a charged amino acid reduces aggregation in a formulation caused, for example, by storage, exposure to elevated temperatures, exposure to light, exposure to shear stress, the presence of surfactants, pH and ionic conditions, and any combinations thereof.

This measure found by the present inventors may be used to decrease aggregation of CD-RAP proteins formulated, in particular in liquid form. The reduced aggregation is thus preferably observed in a liquid formulation. It is assumed that a reduced aggregation may also be observed when stored directly in liquid form for later use, stored in a frozen state and thawed prior to use, or prepared in a dried form, such as a lyophilized, air-dried, or spray-dried form, for later reconstitution into a liquid form or other form prior to use.

Thus, it is envisaged that a formulation described herein may be stored by any method known to one of skill in the art. Non-limiting examples include freezing, lyophilizing, and spray drying the formulation.

In some cases, the protein formulations are frozen for storage. Accordingly, it is desirable that the formulation be relatively stable under such conditions, including under freeze-thaw cycles. One method of determining the suitability of a formulation is to subject a sample formulation to at least two, e.g., three to ten cycles of freezing and thawing (for example by fast thaw at room temperature or slow thaw on ice), determining the amount of low molecular weight (LMW) species and/or high molecular weight (HMW) species that accumulate after the freeze-thaw cycles and comparing it to the amount of LMW species or HMW species present in the sample prior to the freeze-thaw procedure. An increase in the LMW or HMW species indicates decreased stability of a protein stored as part of the formulation. Size exclusion high performance liquid chromatography (SEC-HPLC) can be used to determine the presence of LMW and HMW species.

In some cases, the protein formulations may be stored as a liquid. Accordingly, as described herein, it is desirable that the liquid formulation be stable under such conditions, including at various temperatures. For example, one method of determining the suitability of a formulation is to store the sample formulation at several temperatures (such as 2-8, 15, 20, 25, 30, 35, 40, and 50° C.) and monitoring the amount of HMW and/or LMW species that accumulate over time. The smaller the amounts of HMW and/or LMW species that accumulate over time, the better the storage condition for the formulation. Additionally, the charge profile of the protein may be monitored by cation exchange-high performance liquid chromatography (CEX-HPLC). Alternatively, formulations can be stored after lyophilization.

The term "lyophilized" or "freeze-dried" includes a state of a substance that has been subjected to a drying procedure such as lyophilization, where at least 90% preferably 95%, most preferably 98% of moisture has been removed. Accordingly, the term "lyophilization" as used herein, refers to a process by which the material to be dried is first frozen followed by removal of the ice or frozen solvent by sublimation in a vacuum environment. An excipient (e.g., lyoprotectant) may be included in formulations that are to be lyophilized so as to enhance stability of the lyophilized product upon storage. The term "reconstituted formulation" as used herein, refers to a formulation that has been prepared by dissolving a lyophilized protein formulation in a diluent such that the protein is dispersed in the diluent.

The term "diluent" as used herein, is a substance that is pharmaceutically acceptable (safe and non-toxic for administration to a human) and is useful for the preparation of a liquid formulation, such as a formulation reconstituted after lyophilization. Non-limiting examples of diluents include sterile water, bacteriostatic water for injection (BWFI), a pH buffered solution (e.g., phosphate-buffered saline), sterile saline solution, Ringer's solution, dextrose solution, or aqueous solutions of salts and/or buffers.

Testing a formulation for the stability of the protein component of the formulation after lyophilization is useful for determining the suitability of a formulation. The method is similar to that described above for freezing, except that the sample formulation is lyophilized instead of frozen, reconstituted using a diluent, and the reconstituted formulation is tested for the presence of LMW species and/or HMW species. An increase in LMW or HMW species in the lyophilized sample compared to a corresponding sample formulation that was not lyophilized indicates decreased stability in the lyophilized sample.

In some cases, a formulation is spray-dried and then stored. For spray-drying, a liquid formulation is aerosolized in the presence of a dry gas stream. Water is removed from the formulation droplets into the gas stream, resulting in dried particles of the drug formulation. Excipients may be included in the formulation to (i) protect the protein during the spray-drying dehydration, (ii) protect the protein during storage after spray-drying, and/or iii) give the solution properties suitable for aerosolization. The method is similar to that described above for freezing, except that the sample formulation is spray-dried instead of frozen, reconstituted in a diluent, and the reconstituted formulation is tested for the presence of LMW species and/or HMW species. An increase in LMW or HMW species in the spray-dried sample compared to a corresponding sample formulation that was not lyophilized indicates decreased stability in the spray-dried sample.

Lyophilized formulations are typically reconstituted for use by addition of an aqueous solution to dissolve the lyophilized formulation. A wide variety of aqueous solutions can be used to reconstitute a lyophilized formulation. Preferably, lyophilized formulations are reconstituted using water. Lyophilized formulations are preferably reconstituted with a solution consisting essentially of water (e.g., USP WFI, or water for injection (WFI)) or bacteriostatic water (e.g., USP WFI with 0.9% benzyl alcohol). However, solutions comprising buffers and/or excipients and/or one or more pharmaceutically acceptable carries can also be used.

Freeze-dried or lyophilized formulations are typically prepared from liquids that is, from solutions, suspensions, emulsions, and the like. Thus, the liquid that is to undergo freeze-drying or lyophilization preferably comprises all components desired in a final reconstituted liquid formulation. As a result, when reconstituted, the freeze-dried or lyophilized formulation will render a desired liquid formulation upon reconstitution.

In another aspect of the invention, the formulation is envisaged for use in therapy. Accordingly, the invention envisages a pharmaceutical composition (or medicament) comprising the formulation described herein.

In yet another embodiment, the invention provides a method of treating a subject comprising administering a therapeutically effective amount of the formulation described herein, wherein the subject has a disease or disorder that can be beneficially treated with a CD-RAP polypeptide.

Preferably, the formulation described herein is applied in the prophylaxis and/or treatment of a disease that can be prevented and/or treated with CD-RAP.

The term "subject" is intended to include living organisms. Examples of subjects include mammals, e.g., humans, dogs, cows, horses, pigs, sheep, goats, cats, mice, rabbits, rats, and transgenic non-human animals. In preferred embodiments of the invention, the subject is a human.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the infection and the general state of the subject's own immune system. The term "patient" includes human and other mammalian subjects that receive either prophylactic or therapeutic treatment.

The appropriate dosage, or therapeutically effective amount, of the formulation will depend on the condition to be treated, the severity of the condition, prior therapy, and the patient's clinical history and response to the therapeutic agent. The proper dose can be adjusted according to the judgment of the attending physician such that it can be administered to the patient one time or over a series of administrations. The pharmaceutical composition can be administered as a sole therapeutic or in combination with additional therapies as needed.

The pharmaceutical compositions of this invention are particularly useful for parenteral administration, i.e., subcutaneously, intramuscularly, intravenously, intra-articular and/or intra-synovial. Parenteral administration can be by bolus injection or continuous infusion.

In a preferred embodiment, the injection is a local or non-systemic injection, preferably into the synovia, synovia space, synovial fluid, or synovial joint, subchondral area, osteochondral defect, intra-articular space preferably of the knee, shoulder, hip, thumb, temporomandibular joint or facet joint, annulus fibrosus, nucleus pulposus, nucleus pulposus space, intradiscally or transdically. More preferably, the injection is an intra-articular injection preferably into the knee, shoulder, hip, thumb, temporomandibular joint or facet joint. Further preferably, the intra-articular injection is an intra-articular injection into the synovial fluid of the facet joint or the temporomandibular joint. A further preferred injection is an injection into the subsynovial room or area or an injection into the chondral or osteochondral defect. Also encompassed is an injection into the chondral or osteochondral defect before or after closure of the defect with a membrane. The membrane can be, but is not limited to, a periosteum or a collagen membrane. In another preferred embodiment the membrane is a membrane comprising of collagen type I, collagen type III, porcine or rat collagen type I or type III, hyaluronic acid or derivative thereof. An advantage of the closure of the defect before injection of the formulation is to reduce dilution of the formulation or to increase the local concentration of the active ingredient of the formulation. The membrane further acts as bioadhesive agent for the attachment of cells.

If the protein formulation has been lyophilized, the lyophilized material is first reconstituted in an appropriate liquid prior to administration. The lyophilized material may be reconstituted in, e.g., bacteriostatic water for injection (BWFI), physiological saline, phosphate buffered saline (PBS), an aqueous solution, or the same formulation the protein had been in prior to lyophilization.

Pharmaceutical compositions for injection may be presented in unit dosage form, e.g., in ampoules or in multi-dose containers, with an added preservative. In addition, a number of recent drug delivery approaches have been developed and the pharmaceutical compositions of the present invention are suitable for administration using these new methods, e. g., Inject-ease, Genject, injector pens such as Genen, and needleless devices such as MediJector and BioJector. The present pharmaceutical composition can also be adapted for yet to be discovered administration methods. See also Langer, 1990, Science, 249: 1527-1533.

The pharmaceutical composition can also be formulated as a depot preparation. Such long acting formulations may be administered by implantation (for example subcutaneously, into the ligament or tendon, subsynovially or intramuscularly), by subsynovial injection or by intramuscular injection. Thus, for example, the formulations may be modified with suitable polymeric or hydrophobic materials (for example as a emulsion in an acceptable oil) or ion exchange resins, or as sparingly soluble derivatives, for example, as a sparingly soluble salt. The pharmaceutical compositions may also be in a variety of conventional depot forms employed for administration to provide reactive compositions. These include, for example, solid, semi-solid and liquid dosage forms, such as liquid solutions or suspensions, slurries, gels, creams, balms, emulsions, lotions, powders, sprays, foams, pastes, ointments, salves, balms and drops.

The pharmaceutical compositions may, if desired, be presented in a vial, pack or dispenser device which may contain one or more unit dosage forms containing the active ingredient. In one embodiment the dispenser device can comprise a syringe having a single dose of the liquid formulation ready for injection. The syringe can be accompanied by instructions for administration.

The pharmaceutical composition may further comprise additional pharmaceutically acceptable components. Other pharmaceutically acceptable carriers, excipients, or stabilizers, such as those described in Remington's Pharmaceutical Sciences 16th edition, Osol, A. Ed. (1980) may also be included in a protein formulation described herein, provided that they do not adversely affect the desired characteristics of the formulation. As used herein, "pharmaceutically acceptable carrier" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are non-toxic to recipients at the dosages and concentrations employed and include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counter-ions, such as sodium, polyhydric sugar alcohols; amino acids, such as alanine, glycine, asparagine, 2-phenylalanine, and threonine; sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as glutathione, thioctic acid, sodium thioglycolate, thioglycerol, [alpha]-monothioglycerol, and sodium thio sulfate; low molecular weight proteins, such as humanserum albumin, bovine serum albumin, gelatine, or other immunoglobulines; and hydrophilic polymers, such as polyvinylpyrrolidone.

The formulations described herein are useful as pharmaceutical compositions in the treatment and/or prevention of a disease, or disorder in a patient in need thereof. The term "treatment" refers to both therapeutic treatment and prophylactic or preventative measures. Treatment includes the application or administration of the formulation to the body, an isolated tissue, or cell from a patient who has a disease/disorder, a symptom of a disease/disorder, or a predisposition toward a disease/disorder, with the purpose to cure, heal, alleviate, relieve, alter, remedy, ameliorate, improve, or affect the disease, the symptom of the disease, or the predisposition toward the disease.

Those "in need of treatment" include those already with the disorder, as well as those in which the disorder is to be prevented. The term "disorder" is any condition that would benefit from treatment with the protein formulation described herein. This includes chronic and acute disorders or diseases including those pathological conditions that predispose the mammal to the disorder in question. Non-limiting examples of disorders to be treated herein include degenerative diseases, bone and/or cartilage and/or articular cartilage defect, an immunological disease preferably chronic inflammation of a joint, bone or cartilage tissue such as arthritis (including but not limited to osteoarthritis, rheumatoid arthritis) and a spinal disorder such as degenerative disc disease. In a preferred embodiment the spinal disorder is idiopathic low back pain, disc herniation, internal disc disruption or fissured discs, radiculopathy, spinal stenosis, herniated nucleus pulposus-induced sciatica, sciatica, idiopathic scoliosis or myelopathy.

The term "degenerative diseases" means diseases or defects with impaired cartilage structure such as cartilage degeneration or destruction with or without involvement of bony structures. Preferably, degenerative diseases are degenerative cartilage diseases. These include temporomandibular joint disorder (TMDs), acetabular labrum disorders, arthritis, osteoarthritis, rheumatoid arthritis, psoriatic arthritis, juvenile chronic arthritis, rhizomelic pseudoarthritis, rheumatoid polyarthritis, degenerative disc disease, chondral or osteochondral defects, focal chondral defect, focal osteochondral defect, superficial chondral defects, osteochondritis dissecans, full-thickness chondral defects, partial-thickness chondral defects, chondromalacia, traumas associated with the tendons and ligaments in and around the knee joint, trauma of the lateral or medial meniscus, meniscus tears, anterior crucial ligament injury, synovial osteochondromatosis, spondylitis, ankylosing spondylitis, synovitis, villonodulat synovitis.

The term "cartilage defect" refers to any cartilage abnormality including cartilage diseases, alteration of cartilage caused e.g. by trauma or degenerative processes.

The term "articular cartilage" covers the surface of the portion of bones in joints and functions as a cushion between two bones to allow movement in joints. Normal healthy articular cartilage is described as hyaline cartilage. Articular cartilage consists of specialized cells (chondrocytes) embedded into a matrix of intracellular material rich in proteoglycans, predominantly aggrecan, collagen type II fibrils, other proteins and water. The matrix is produced and maintained by the chondrocytes embedded within. Cartilage tissue is not innervated and vascularised and is nourished by the underlying tissue.

In addition to the CD-RAP protein, the pharmaceutical composition of the invention can comprise additional therapeutic or biologically-active agents. For example, therapeutic factors useful in the treatment of a particular indication e.g. osteoarthritis such as one or more inhibtors that are involved in destruction of articular cartilage or synovial components not limited to anti-metalloproteinases, cycline compounds, cytokine antagonists, corticosteroids, TNF inhibitors, IL-inhibitors, anti-angiogenic substances, aggrecanase inhibitors, p38 kinase inhibitors, apoptosis inhibitors, hyaluronidase inhibitors and inhibitors of proteolytic enzymes can be present. Factors that control inflammation including infliximab, etanercerpt, adalimulab, nerelimonmab, lenercerpt and the like, or combinations thereof can also be part of the composition. It is also envisaged that the pharmaceutical liposomal composition may include extracellular matrix components such as hyaluronic acid or a derivative thereof including salts, ester, inner ester and sulphated derivates, preferably partial ester of hyaluronic acid.

In another embodiment, the present invention is directed to a kit (or article of manufacture) or container, which contains a formulation of the invention. The formulation may preferably already be in a liquid state. However, alternatively, it may preferably be in a lyophilized state. It may also be in a frozen, lyophilized, freeze-dried or spray-dried state. Accordingly, if the formulation is in state other than liquid, it can be prepared by the practitioner as (liquid) aqueous pharmaceutical composition. For example, the formulation may be lyophilized and would then have to be reconstituted. Accordingly, the kit may further comprise means for the reconstitution of a frozen, lyophilized, freeze-dried or spray-dried formulation and/or means for diluting the formulation and/or means for administering the formulation or pharmaceutical composition, respectively. The kit can also be accompanied by instructions for use.

Thus, an article of manufacture is provided which contains a formulation described herein and preferably provides instructions for its use. The article of manufacture comprises a container suitable for containing the formulation. Suitable containers include, without limitation, bottles, vials (e.g., dual chamber vials), syringes (e.g., single or dual chamber syringes), test tubes, nebulizers, inhalers (e.g., metered dose inhalers or dry powder inhalers), or depots. The container can be formed from a variety of materials, such as glass, metal or plastic (e.g., polycarbonate, polystyrene, polypropylene, polyolefine). The container holds the formulation and the label on, or associated with, the container may indicate directions for reconstitution and/or use. The label may further indicate that the formulation is useful or intended for subcutaneous administration. The container holding the formulation may be a multi-use vial, which allows for repeat administrations (e.g., from 1-6 administrations) of the formulation. The article of manufacture may further comprise a second container comprising a suitable diluent (e.g., WFI, 0.9% NaCl, BWFI, phosphate buffered saline). When the article of manufacture comprises a lyophilized version of a protein formulation, mixing of a diluent with the lyophilized formulation will provide a final protein concentration in the reconstituted formulation of generally at least 20 mg/mL. The article of manufacture may further include other materials desirable from a commercial and user standpoint, including other buffers, diluents, filters, needles, syringes, and package inserts with instructions for use.

In another embodiment of the invention, an article of manufacture is provided which contains the aqueous formulation of the present invention and provides instructions for its use. The article of manufacture comprises a container. Suitable containers include, for example, bottles, vials (e.g., dual chamber vials), syringes (such as dual chamber syringes), autoinjector pen containing a syringe, and test tubes. The container may be formed from a variety of materials such as glass, plastic or polycarbonate. The container holds the aqueous formulation and the label on, or associated with, the container may indicate directions for use. For example, the label may indicate that the formulation is useful or intended for subcutaneous administration. The container holding the formulation may be a multi-use vial, which allows for repeat administrations (e.g., from 2-6 administrations) of the aqueous formulation. The article of manufacture may further comprise a second container. The article of manufacture may further include other materials desirable from a commercial and user standpoint, including other buffers, diluents, filters, needles, syringes, and package inserts with instructions for use.

Also included in the invention are devices that may be used to deliver the formulation of the invention. Examples of such devices include, but are not limited to, a syringe, a pen, an implant, a needle-free injection device, an inhalation device, and a patch.

The invention is further illustrated by the Figures and Examples which are merely illustrative and are not constructed as a limitation of the scope of the present invention.

The Figures show:

FIG. 1: Factors influencing protein stability

Figure 2:
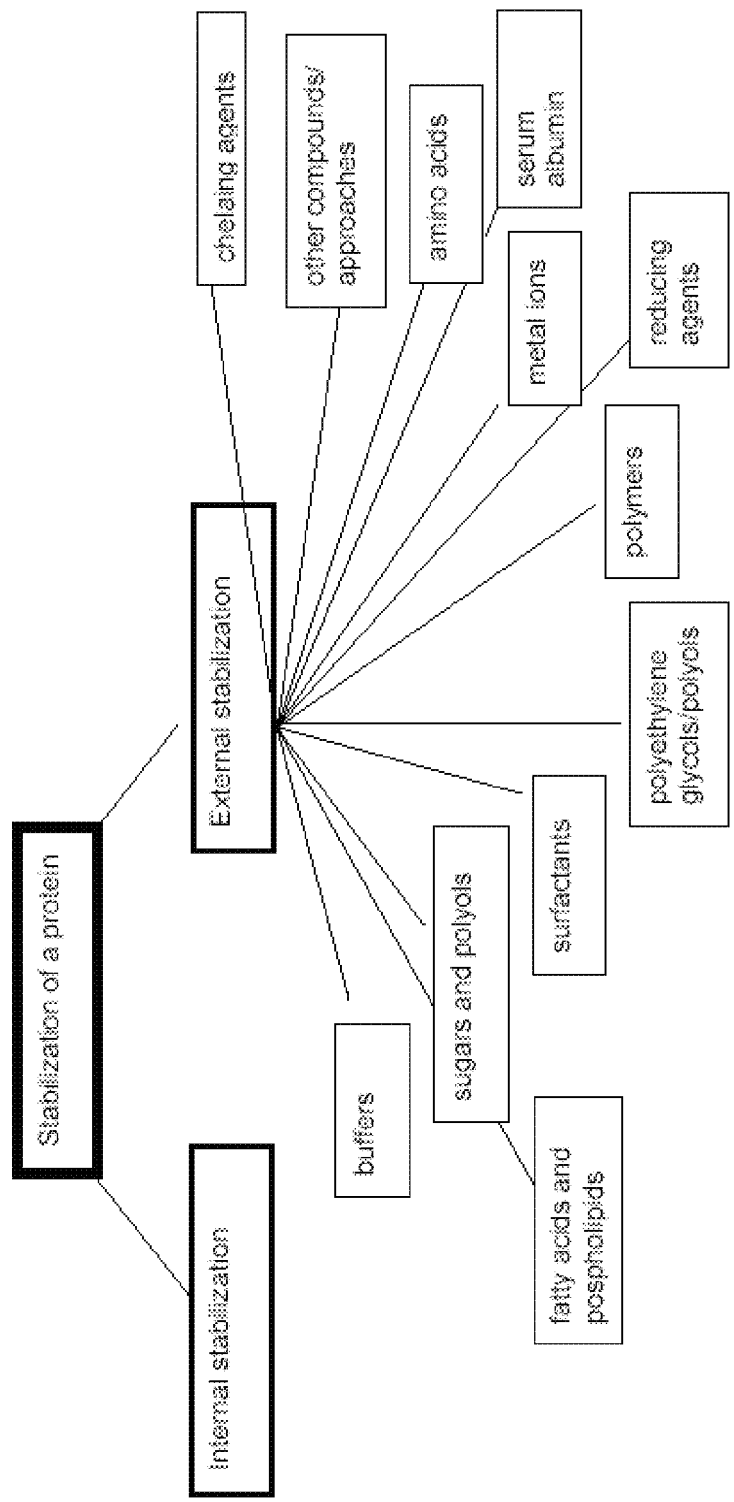

FIG. 2: Exemplary measures that can be taken to stabilize a protein

Figure 3:
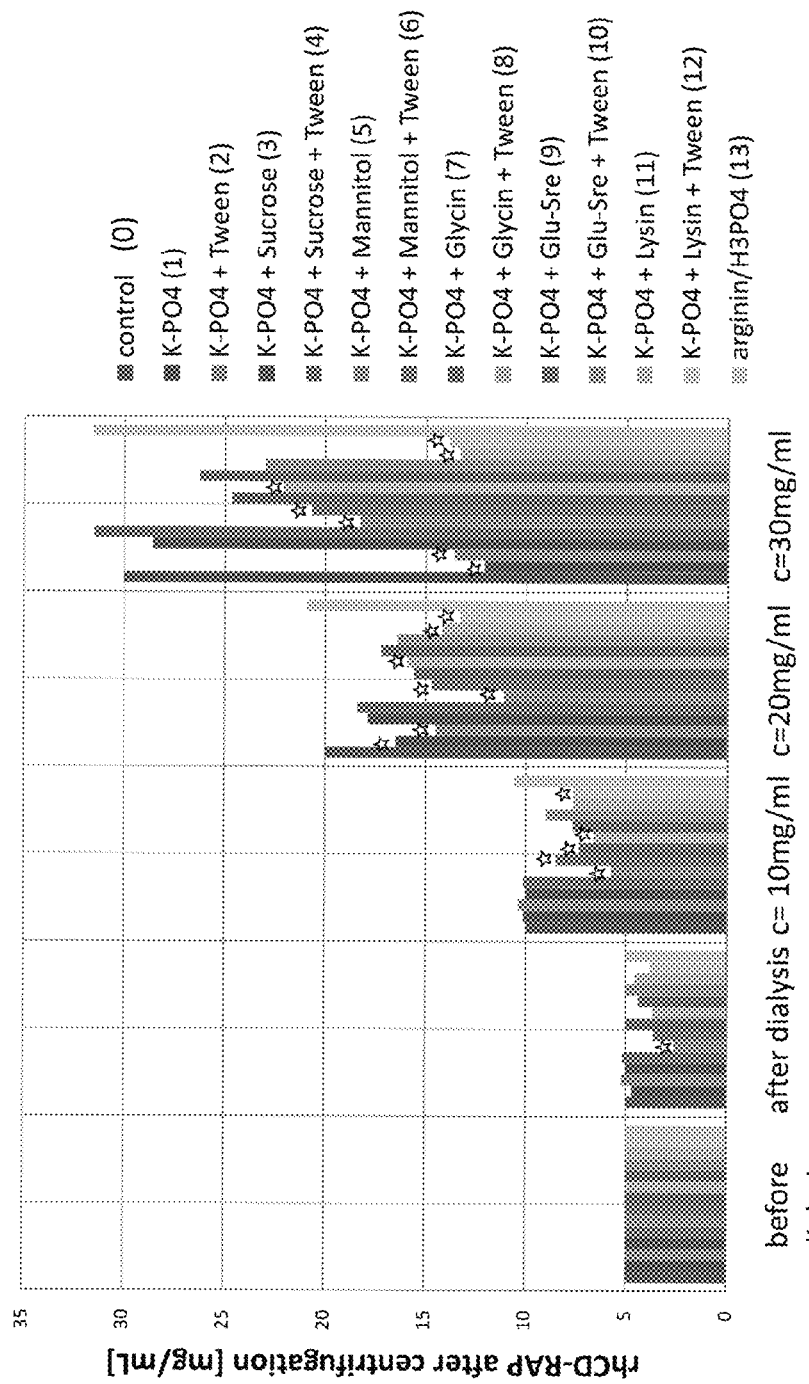

FIG. 3: Successive concentration of rhCD-RAP in potassium phosphate.

Figure 4:
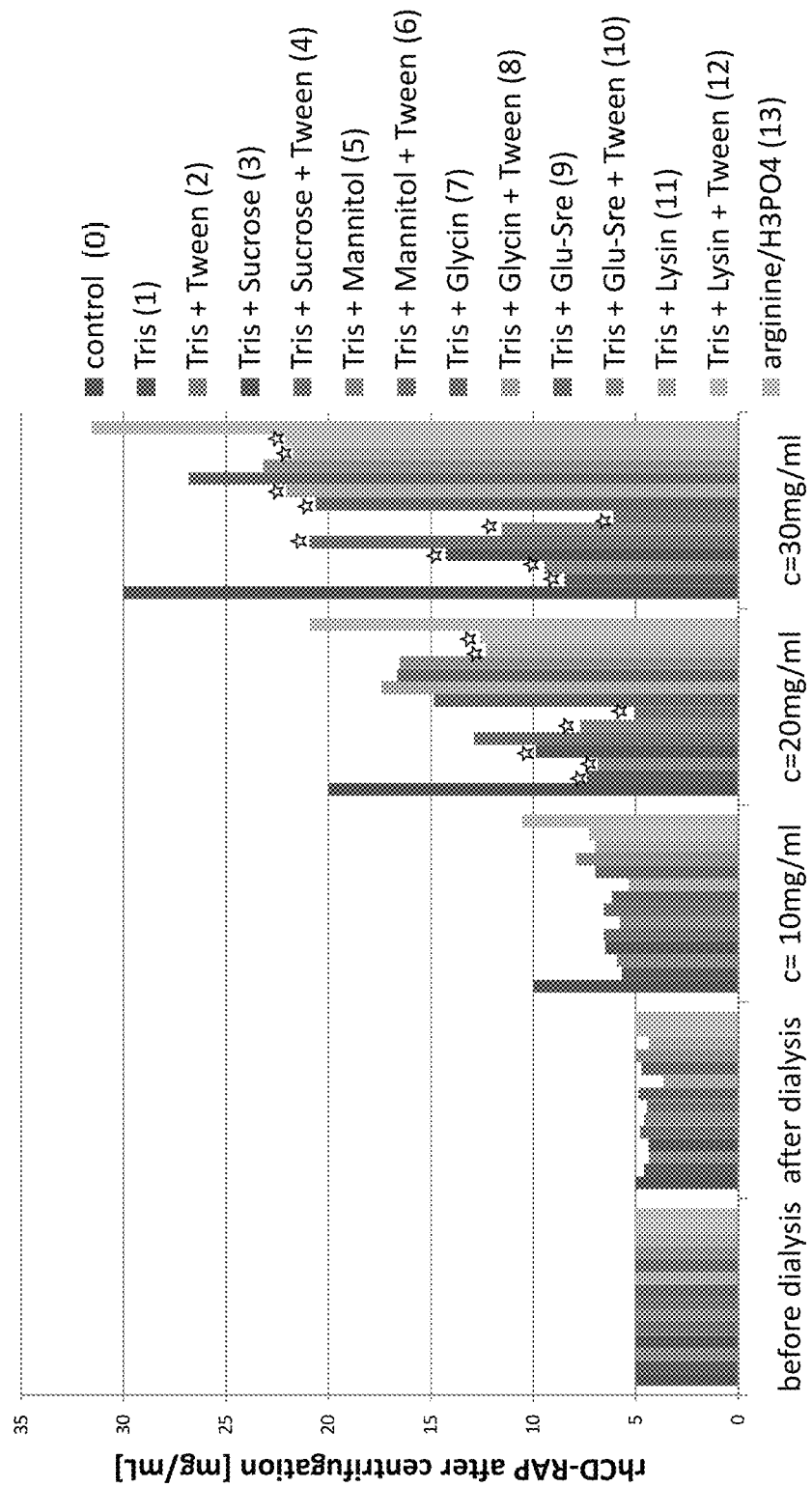

FIG. 4: Successive concentration of rhCD-RAP in TRIS chloride

Figure 5:
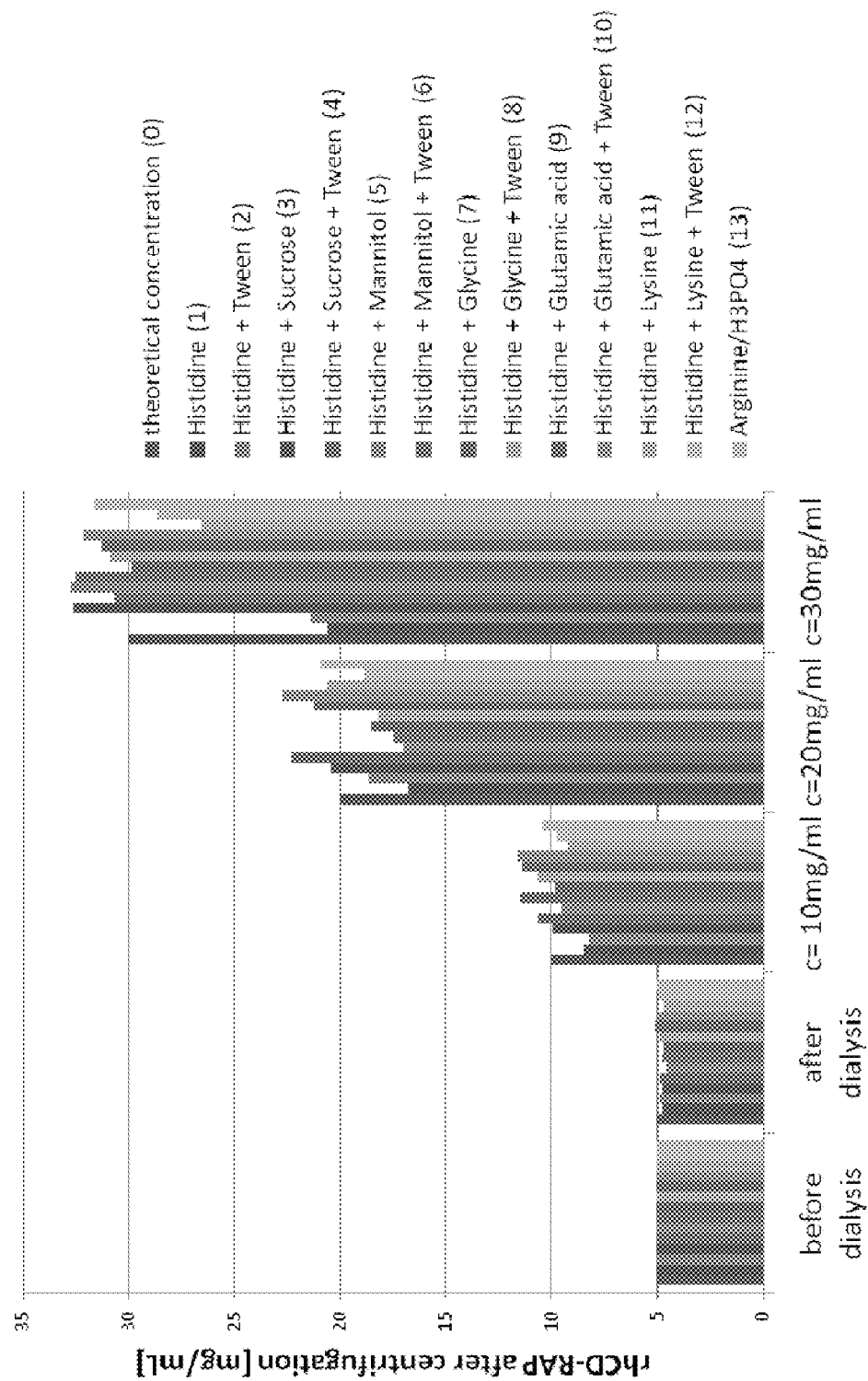

FIG. 5: Successive concentration of rhCD-RAP in Histidine chloride

Figure 6:
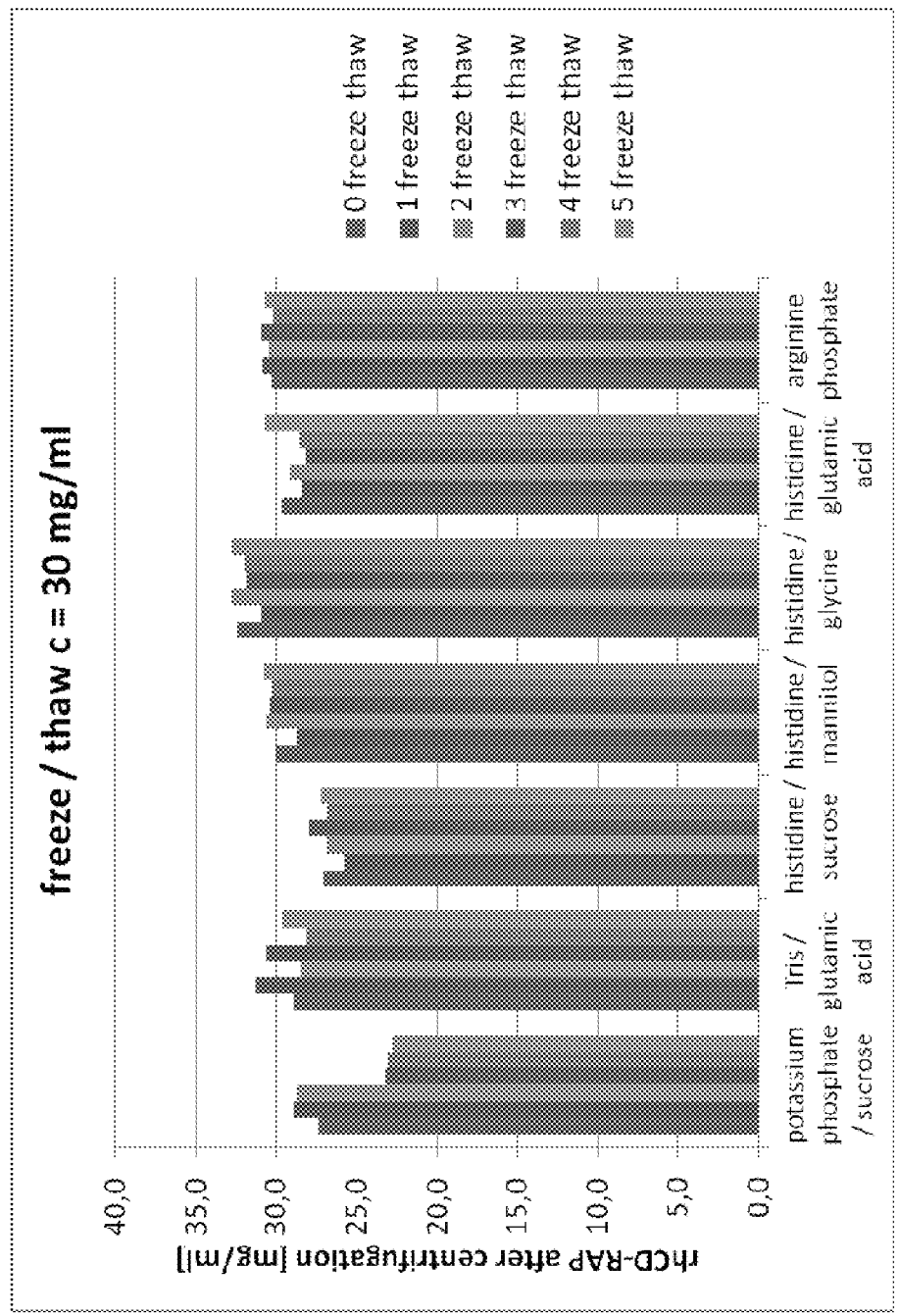

FIG. 6: Stability of rhCD-RAP in high concentration in different buffer systems

Figure 7:
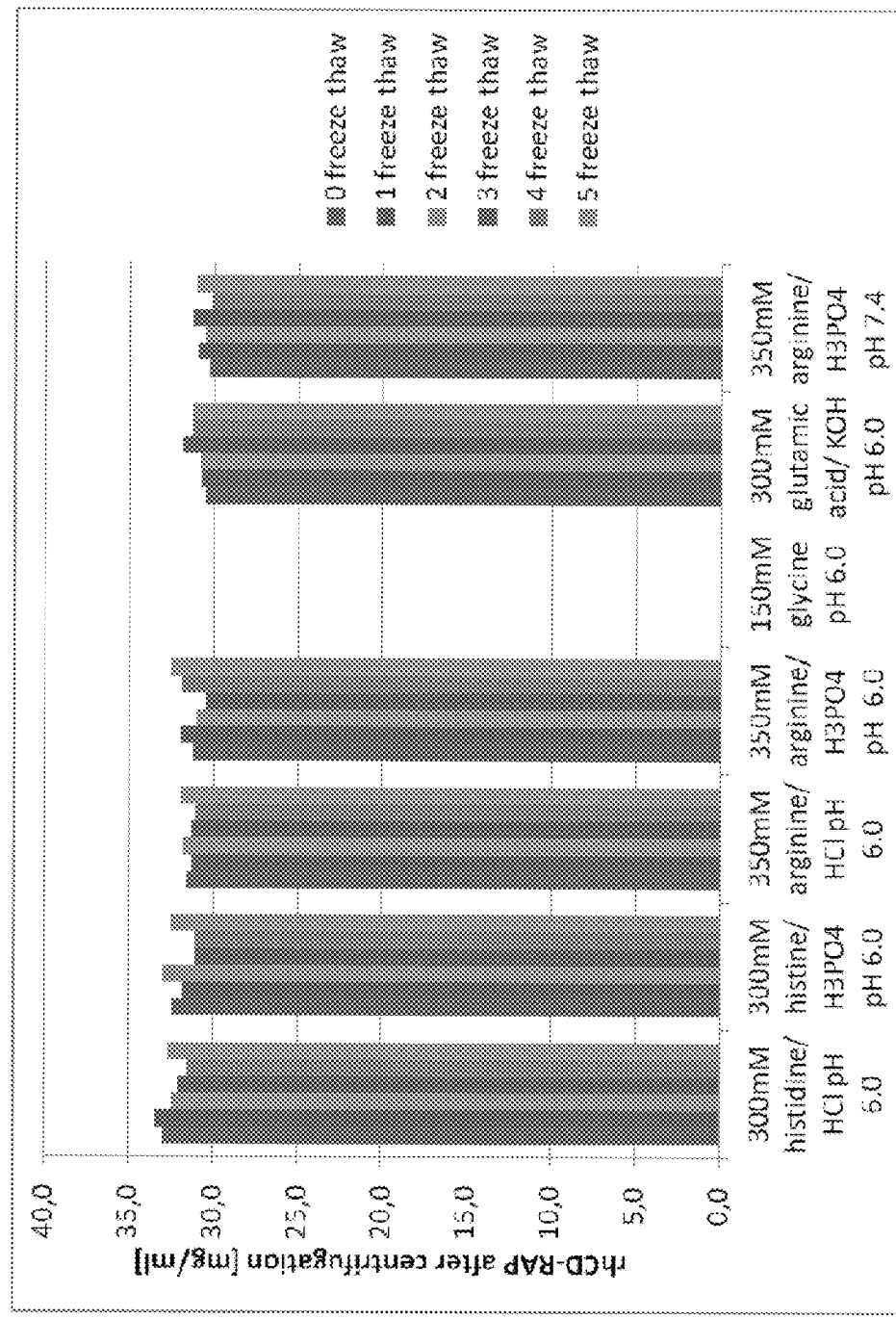

FIG. 7: Stability of rhCD-RAP in high concentration in different buffer systems

Figure 8:
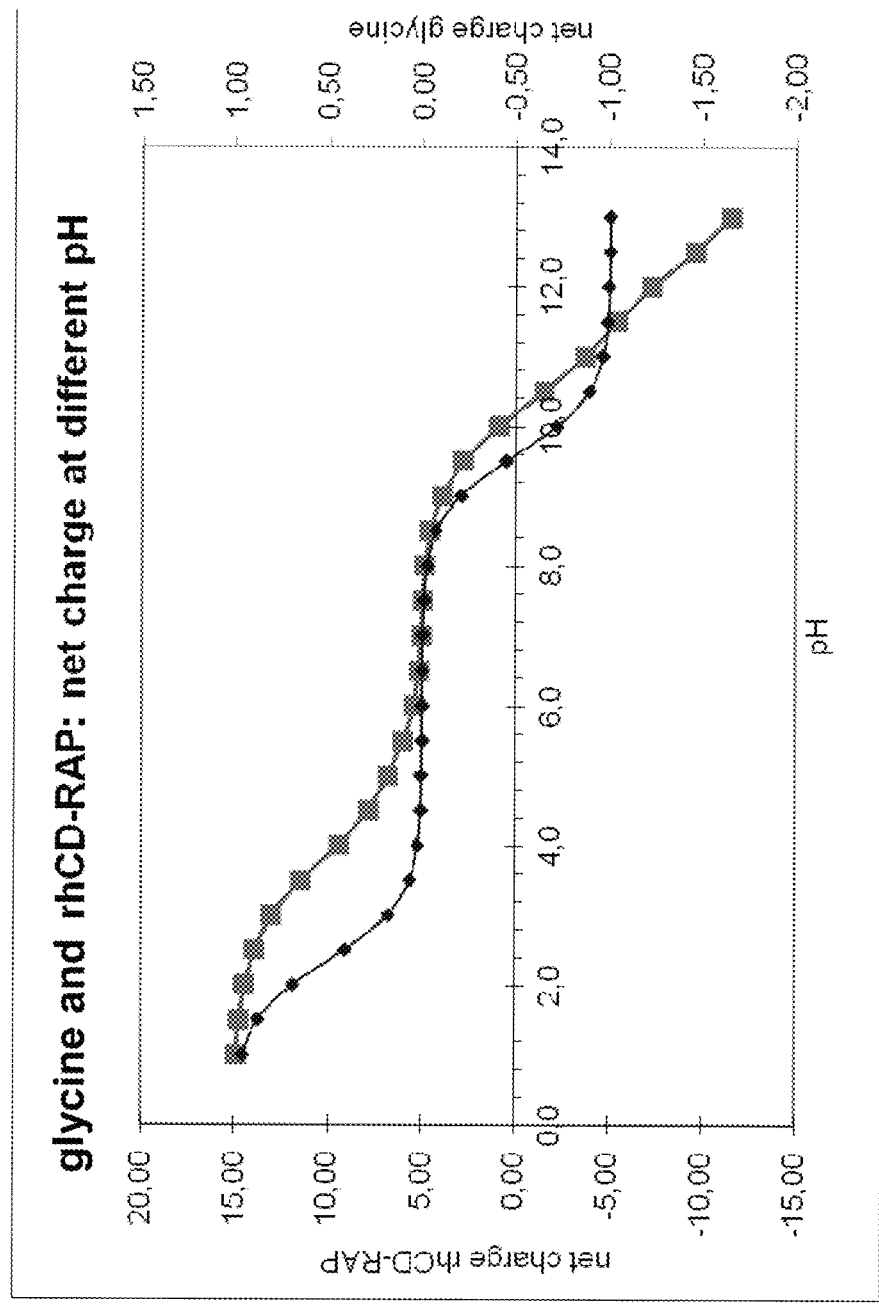

FIG. 8: Net charge of glycine and rhCD-RAP at different pH values

Figure 9:
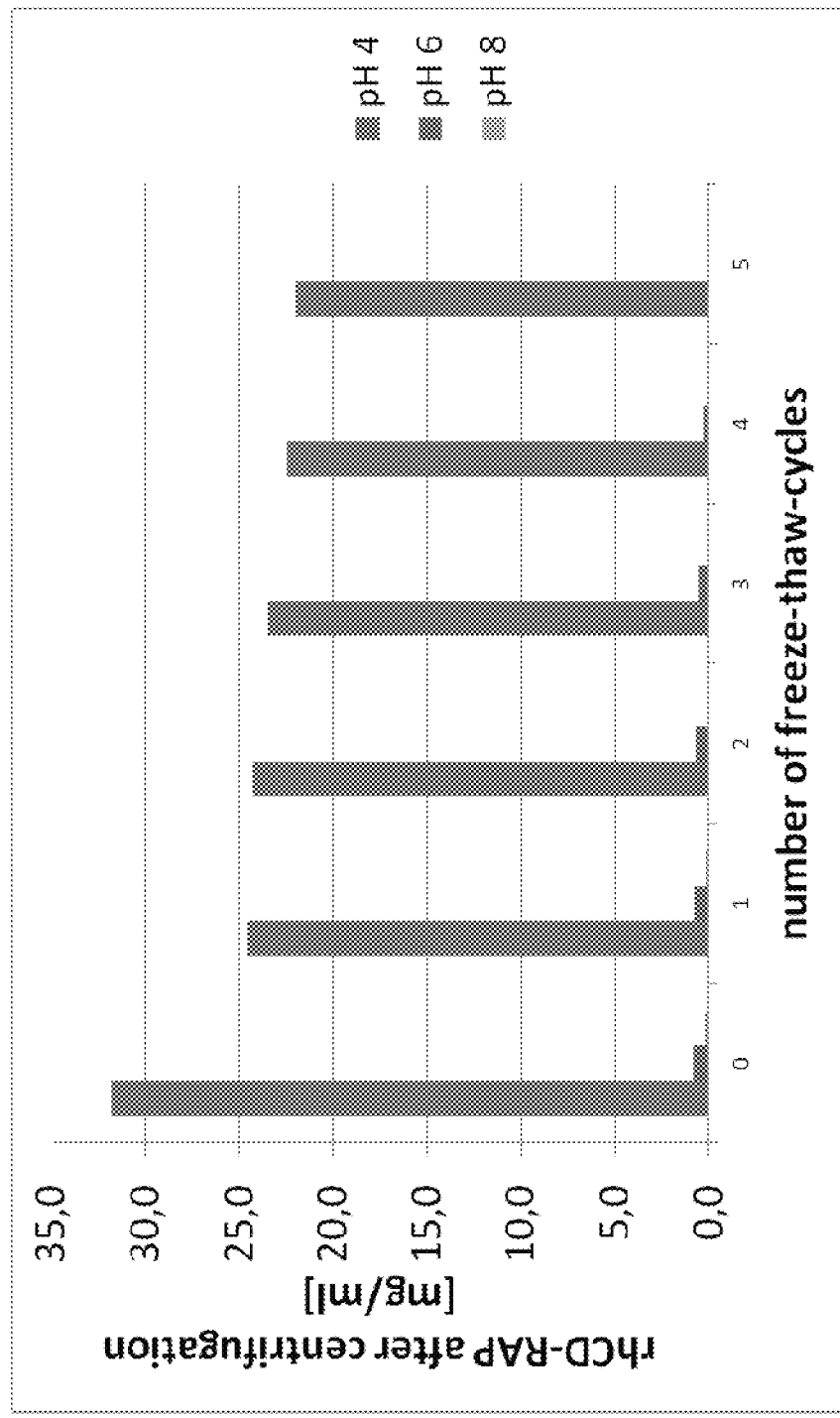

FIG. 9: Influence of pH on solubility of rhCD-RAP in 150 mM glycine

Figure 10:
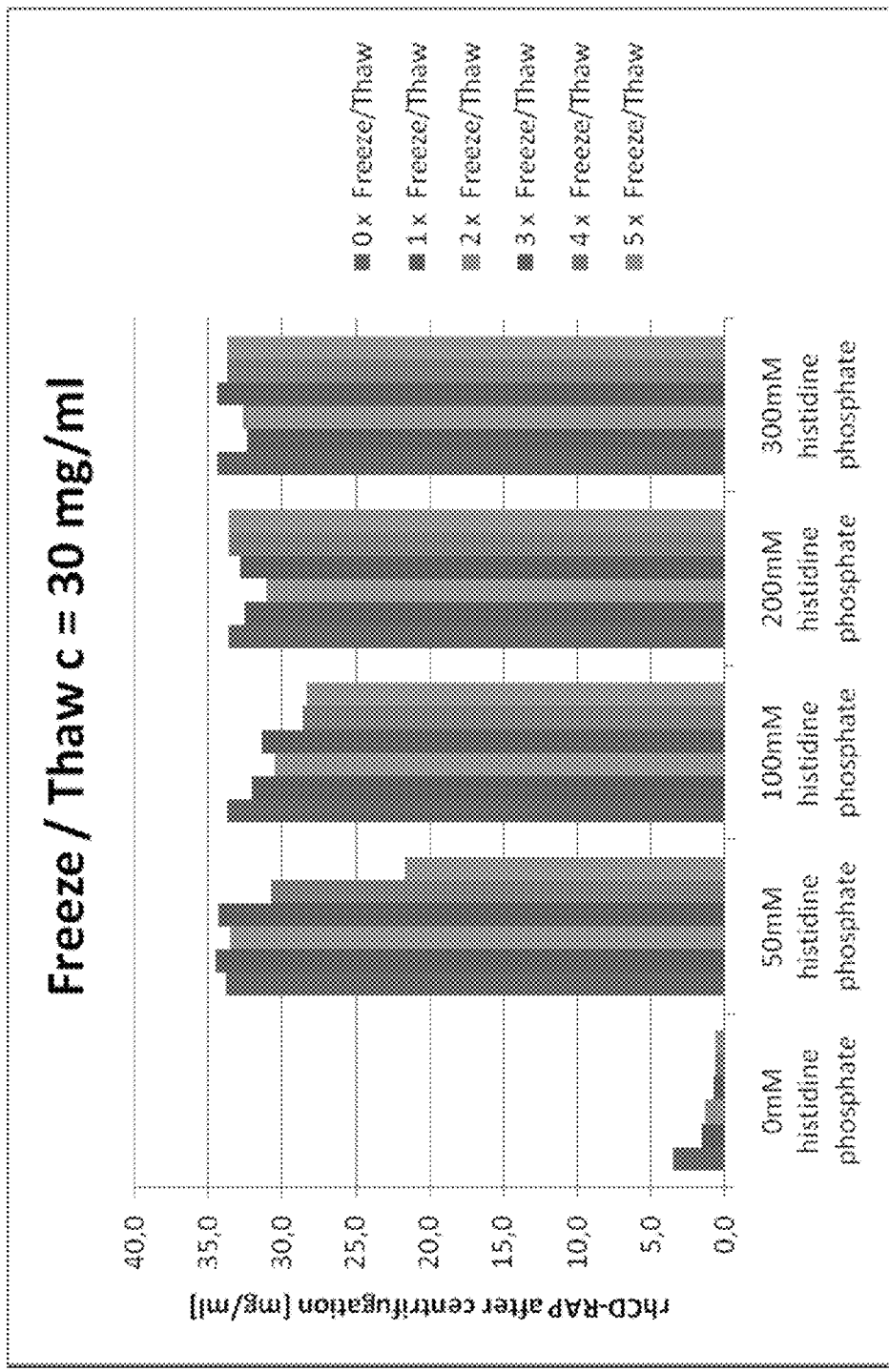

FIG. 10: Influence of histidine phosphate molarity on solubility of rhCD-RAP

Figure 11:
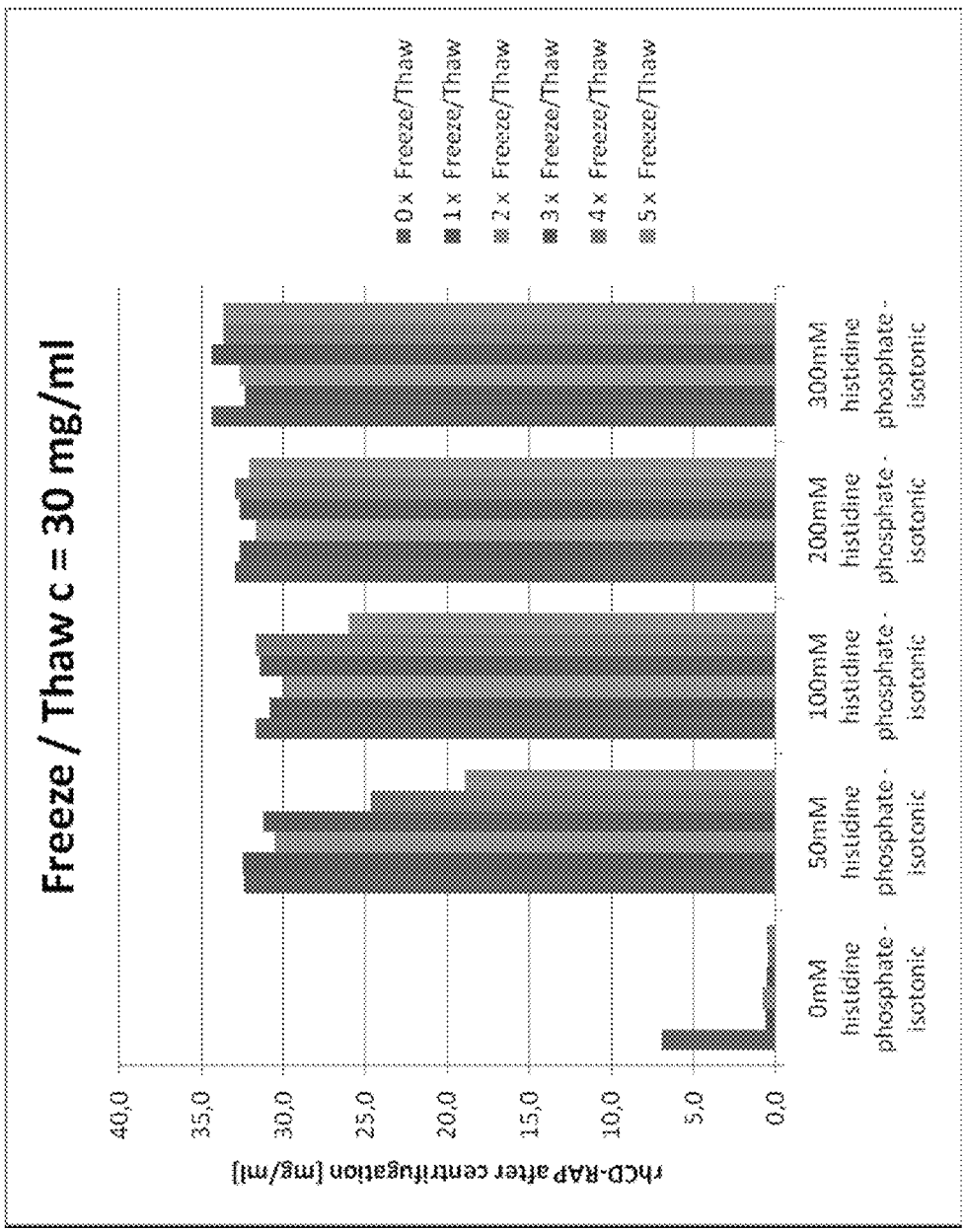

FIG. 11: Influence of histidine phosphate (adjusted to isotonic osmolatity with potassium chloride) on rhCD-RAP solubility Please note that in FIGS. 3-11, the numbering added to the legend of the bar chart pertains to the bars of each "block" shown in the chart (from left to right). For example, "0" pertains to the outer left bar, "1" pertains to the bar next to the bar denoted with"0", etc.

The following Examples illustrate the invention.

Based on the inventors' consideration aiming at stable formulations of high concentrations of CD-RAP so as to enable lower volume injection for patients, which reduces side effects like pain due to high volume injection, various formulations were tested on their effect on CD-RAP protein stabilization. Some of these formulations are exemplarily shown in the following examples below. However, as mentioned herein, when starting with the inventors' aim, it is a matter of empirical work to find the proper ingredients of a formulation that meets the aim, since each protein has different properties and thus, one cannot conclude from one example which ingredients are the proper ones.

EXAMPLE 1

Various Buffer Systems were Analysed for rhCD-RAP rhCD-RAP was dialyzed against 36 buffer systems (50 mM potassium chloride, 50 mM histidine chloride or 50 mM TRIS chloride each pH 6.0, each buffer with or without the addition of one of the following stabilizers selected from sucrose, mannitol, glycine, lysine and glutamic acid either with or without 0.1% Tween® 20. During the subsequent concentration process by dialysis up to 30 mg/mL of rhCD-RAP by filtration samples were analyzed by UV/Vis.

Stable formulations were stressed by freeze-thaw-cycles. After each cycle the samples were centrifuged and rhCD-RAP was quantified by UV/Vis.

Dialysis 2.0 ml of rhCD-RAP bulk material (in 350 mM Arginine/Phosphate pH 7.4) was dialyzed against 500 mL of desired buffer at 4° C. over 24 h under moderate stirring by using a 6-8 kDa molecular weight cut-off tube. After 16 h the dialysis buffer was exchanged with 500 mL of fresh buffer. The resulting protein solutions were stored at 2-8° C. for further analysis.

UV-Vis

Protein content in samples was determined by UV/Vis after centrifugation of the dialyzed rhCD-RAP for 5 minutes at 13.000 rcf. The corresponding sample buffers served for blank subtraction. For calculation of the protein concentration [mg/ml] the absorbance at 280 nm and the specific absorptivity of rhCD-RAP at 280 nm [1.649 mL/(mg*cm)] were used.

Increase of rhCD-RAP-Concentration

Dialyzed rhCD-RAP was transferred into a 2 mL centrifugal concentrator.

After subsequent centrifugation steps (4000 rcf, 4° C.) the volume of rhCD-RAP solution decreased. The volume of the remaining rhCD-RAP solution was determined and rhCD-RAP concentration was quantified by UV/Vis.

Thermal Stability (Freeze/Thaw-Cycles)

Thermal stability of rhCD-RAP was evaluated by applying five freeze/thaw cycles from 5° C. temperature to −25° C. using a deep freezer. Cooling and heating rates were 1.0°

C./min with an isothermal step of 15 min between each cycle. The protein solutions were stored at 4° C.-8° C. until analysis.

300 μl rhCD-RAP in a concentration of 30 mg/mL were transferred into 1.5 mL PP vials and stressed by defined freeze-thaw-steps as described above.

EXAMPLE 2

Stability of rhCD-RAP in Different Buffer Systems

The stabilizing effects of all buffer systems of Example 1 were determined.

Potassium Phosphate Buffer Systems

The following substances were solved in WFI to a final weight of 1 kg giving a buffer concentration of 50 mM. The pH was adjusted to pH 6.0 by addition of KOH and HCl respectively.
 a) 6.8 g potassium phosphate, 12.4 g KCl with and without 1.0 g Tween® 80
 b) 6.8 g potassium phosphate, 50 g sucrose, 4.9 g KCl with and without 1.0 g Tween® 80
 c) 6.8 g potassium phosphate, 50 g mannitol, with and without 1.0 g Tween® 80
 d) 6.8 g potassium phosphate, 25 g glycine, with and without 1.0 g Tween® 80
 e) 6.8 g potassium phosphate, 25 g glutamic acid, with and without 1.0 g Tween® 80
 f) 6.8 g potassium phosphate, 25 g lysine, with and without 1.0 g Tween® 80
 g) 61.0 g arginin, pH 7.4 adjusted with phosphoric acid (control)

Isotonicity of 300-400 mOsm/kg was adjusted with potassium chloride, if it became necessary. The osmolality of each buffer is shown in Table 1.

TABLE 1

Osmolality of potassium phosphate buffers

| formulation | osmolality [mOsm/kg] |
|---|---|
| 50 mM Potassium phosphate | 345 |
| 50 mM Potassium phosphate + 5% (w/v) Sucrose | 340 |
| 50 mM Potassium phosphate + 5% (w/v)Mannitol | 376 |
| 50 mM Potassium phosphate + 2.5% (w/v) Glycine | 371 |
| 50 mM Potassium phosphate + 2.5% (w/v) Glutamic acid | 354 |
| 50 mM Potassium phosphate + 2.5% (w/v) Lysine | 302 | rhCD-RAP was then dialyzed against potassium phosphate based buffer systems as listed in Table 1 and concentrated by centrifugation in filtration units. After defined successive reduction of buffer the sustained volume of protein solution was determined and rhCD-RAP concentration was quantified by UV/Vis. FIG. 3 shows the resulting concentration of CD-RAP before and after dialysis of a 5 mg/mL CD-RAP solution as well as after concentration to 10, 20 and 30 mg/mL. The arginine/phosphate buffer served as a control.

As shown in FIG. 3 the formulation in the arginine/phosphate buffer system showed optimal solubility in all concentration steps. Even in the highest concentration step the measured protein content reached the theoretical content of rhCD-RAP. Thus since there was no loss of protein in arginine/phosphate for rhCD-RAP this buffer is one of the most preferred solubilisation solutions.

In contrast to arginine/phosphate the use of potassium phosphate as formulation buffer required some extra supplements for reaching sufficient solubility. As 50 mM of potassium phosphate (comprising potassium chloride as ionic supplement for reaching isotonic status) showed good solubility only up to 10 mg/mL rhCD-RAP, there was a need for the addition of supplements in order to achieve solubility at concentration levels of up to 30 mg/mL rhCD-RAP and higher. From the wide range of stabilizers only sucrose leads to an excellent solubility of rhCD-RAP even at a concentration of 30 mg/mL. Others showed aggregation effects with partially visible precipitated protein at different concentration steps.

Tris Buffer Systems

TRIS chloride in variation with stabilizers like sucrose, mannitol, glycine, glutamic acid and lysine, with or without Tween80® as solubility enhancer were solved in WFI to a final weight of 1 kg, giving a buffer concentration of 50 mM. The pH was adjusted to pH 6.0 by using additional HCl respectively.
 a) 6.05 g TRIS base, 9.7 g NaCl with and without 1.0 g Tween® 80
 b) 6.05 g TRIS base, 50 g sucrose, 3.9 g NaCl with and without 1.0 g Tween® 80
 c) 6.05 g TRIS base, 50 g mannitol, with and without 1.0 g Tween® 80
 d) 6.05 g TRIS base, 25 g glycine, with and without 1.0 g Tween® 80
 e) 6.05 g TRIS base, 25 g glutamic acid, with and without 1.0 g Tween® 80
 f) 6.05 g TRIS base, 25 g lysine, with and without 1.0 g Tween® 80

Isotonicity of 300-400 mOsm/kg was adjusted with potassium chloride, if it became necessary. The osmolality of each buffer is shown in Table 2.

TABLE 2

Osmolality of TRIS buffers

| formulation | Osmolality [mOsm/kg] |
|---|---|
| 50 mM TRIS | 342 |
| 50 mM TRIS + 5% Sucrose | 344 |
| 50 mM TRIS + 5% Mannitol | 378 |
| 50 mM TRIS + 2.5% Glycine | 370 |
| 50 mM TRIS + 2.5% Glutamic acid | 350 |
| 50 mM TRIS + 2.5% Lysine | 309 | rhCD-RAP was dialyzed and concentrated up to 30 mg/mL as described for the potassium phosphate buffer above. 350 mM arginine phosphate buffer served as a control for optimal solubility.

Compared to potassium phosphate based buffer formulations all TRIS chloride buffers except 50 mM TRIS chloride with 2.5% glutamic acid showed poor solubility above 5 mg/m LCD-RAP.

Histidine Buffer Systems

Histidine chloride (50 mM, pH 6.0) in variation with stabilizers like sucrose, mannitol, glycine, glutamic acid and lysine, with or without Tween80® as solubility enhancer were analyzed as follows using the same method as described above for the other two buffer systems.
 a) 7.76 g L-histidine chloride, 12.4 g KCl with and without 1.0 g Tween® 80
 b) 7.76 g L-histidine chloride, 50 g sucrose, 4.9 g KCl with and without 1.0 g Tween® 80
 c) 7.76 g L-histidine chloride, 50 g mannitol, with and without 1.0 g Tween® 80 d) 7.76 g L-histidine chloride, 25 g glycine, with and without 1.0 g Tween® 80
e) 7.76 g L-histidine chloride, 25 g glutamic acid, with and without 1.0 g Tween® 80
f) 7.76 g L-histidine chloride, 25 g lysine, with and without 1.0 g Tween® 80

The osmolality was adjusted where necessary. The final osmolality is shown in Table 3.

TABLE 3

Osmolality of histidine chloride buffers

| buffer formulation | osmolality [mOsm/kg] |
|---|---|
| 50 mM Histidine | 348 |
| 50 mM Histidine + 5% Sucrose | 349 |
| 50 mM Histidine + 5% Mannitol | 371 |
| 50 mM Histidine + 2.5% Glycine | 375 |
| 50 mM Histidine + 2.5% Glutamic acid | 355 |
| 50 mM Histidine + 2.5% Lysine | 307 | rhCD-RAP was dialyzed in the buffer systems and concentrated up to 30 mg/mL (compare 4.1.1).

Compared to both potassium phosphate and TRIS based buffer formulations histidine chloride based buffers generated the best solubility results of rhCD-RAP beside the present buffer arginine phosphate.

With the exception that 50 mM histidine +/− Tween80® aggregated above concentrations of 5 mg/mL rhCD-RAP, all other buffers showed a very good solubility of up to 30 mg/mL in an isotonic buffer within a pH of 6.0 and around the neutral pH. Again, there was no effect on the solubility of rhCD-RAP by the use of Tween80® in the buffer systems when analyzed.

CONCLUSION

The best results of CD-RAP providing a high concentration of protein of up to 30 mg/mL without aggregation were the following: a) 50 mM potassium phosphate with 5% sucrose, b) 50 mM TRIS chloride, 2.5% glutamic acid, c) 50 mM histidine, 2.5% glycine, d) 50 mM histidine, 2.5% glutamic acid, e) 50 mM histidine, 2.5% lysine, f) histidine with 5% mannitol and g) 350 mM arginine phosphate.

Dropping the desired concentration to 5 mg/mL for nearly all tested formulations enabled protein stability whereas raising the concentration to 30 mg/mL enabled the hurdle to be cleared.

EXAMPLE 3

Evaluation of Thermal Stability of rhCD-RAP in Different Buffer Systems by Freeze Thaw Cycles Example 1 evaluated 7 buffer formulations for their ability to concentrate rhCD-RAP up to 30 mg/mL at pH 6.0. These formulations were tested to maintain rhCD-RAP stability under stress situations i.e. freeze/thaw cycling.

rhCD-RAP was dialyzed in buffer systems (a) 50 mM potassium phosphate with 5% sucrose, b) 50 mM TRIS chloride, 2.5% glutamic acid, c) 50 mM histidine, 2.5% glycine, d) 50 mM histidine, 2.5% glutamic acid, e) 50 mM histidine, 2.5% lysine, f) histidine with 5% mannitol, g) 350 mM arginine phosphate and subsequently concentrated by centrifugation in filtration units to concentrations of ~30 mg/mL rhCD-RAP. 300 µl were transferred into 1.5 mL PP vials. The formulations were stressed by 5 freeze/thaw cycles, aggregated rhCD-RAP was removed afterwards by centrifugation and the remaining soluble rhCD-RAP was quantified by UV/Vis.

rhCD-RAP was successfully concentrated to around 30 mg/mL in all tested buffer systems.

FIG. 6 shows no negative effect on protein concentration by freeze thaw cycles in all formulations except rhCD-RAP in 50 mM potassium phosphate/5% sucrose. Only when in 50 mM potassium phosphate/5% sucrose could a significant decrease of rhCD-RAP be observed after the third freeze/thaw process and temporarily a cloudy milk like dispersion was visible. In all other formulations the solution was clear after every freeze/thaw cycle, which in combination with the results of the quantification of rhCD-RAP by UV/Vis solved the problem of solubility and stability of rhCD-RAP in high concentrations.

Surprisingly only buffer systems which comprised of at least one amino acid resulted in thermal stability of rhCD-RAP after freeze and thaw cycling.

EXAMPLE 4

Stabilizing Effect of Different Amino Acids on rhCD-RAP (30 mg/mL)

Since Example 2 and 3 showed excellent rhCD-RAP solubility at concentrations of 30 mg/mL in buffer solutions containing amino acids this special amino acid effect was examined in the following Example.

Basic amino acids such as histidine and arginine as well as neutral amino acids such as glycine and acid amino acids such as glutamic acid were tested in their stabilizing effect on rhCD-RAP.

All bulk solutions are designed isotonic at pH 6.0 without addition of any salts or other excipients; pH was adjusted with both hydrochloric acid and phosphoric acid. Additionally 350 mM arginine phosphate was tested at pH 6.0 and pH 7.4.

TABLE 4 rhCD-RAP stressed by freeze thaw cycles in different buffers

| formulation | osmolarity [mOsm/kg] |
|---|---|
| 300 mM L-histidine-chloride pH 6 | 330 |
| 300 mM L-histidine-phosphate pH 6 | 303 |
| 350 mM arginine-chloride pH 6 | 302 |
| 350 mM arginine-phosphate pH 6 | 310 |
| 350 mM arginine-phosphate pH 7.4 | 300 |
| 300 mM potassium-glutamate pH 6 | 337 |
| 150 mM glycine pH 6 | 326 | rhCD-RAP was dialyzed in buffer systems (listed in Table 4) and was subsequently concentrated by centrifugation in filtration units to a concentration of ~30 mg/mL rhCD-RAP. 300 µl were transferred into 1.5 mL PP vials.

The formulations listed in Table 4 were stressed by 5 freeze/thaw cycles according to the Examples above. Aggregated rhCD-RAP was removed afterwards by centrifugation and the remaining soluble rhCD-RAP was quantified by UV/Vis.

FIG. 7 shows excellent stabilizing effect of all tested buffer systems and solubility of rhCD-RAP in freeze/thaw cycles except one: rhCD-RAP dialyzed in 150 mM glycine aggregated quantitatively during the dialyzing step. Thus glycine at pH 6.0 as the only non-charged amino acid analyzed indicates that the charge of the amino acid is an important technical property in the use of amino acids for preparation of rhCD-RAP bulk buffers. However, both phosphate and chloride buffer performed in the same manner.

EXAMPLE 5

Effect of Different pH Upon Solubility of rhCD-RAP in Glycine

Example 4 pointed to a poor solubility of rhCD-RAP in isotonic glycine solutions at pH 6.0 due to its neutral behaviour. The inventors then determined the consequence of the solubility of CD-RAP if glycine is still uncharged but rhCD-RAP comprises a higher net charge due to a change in pH and a higher net charge of CD-RAP respectively.

FIG. 8 illustrates the net charge of both glycine and rhCD-RAP at different pH values due to their pKs values. In this experiment rhCD-RAP was dialyzed against 150 mM glycine at pH 4.0, pH 6.0 and pH 8.0. PH values were adjusted with phosphoric acid and sodium hydroxide respectively. rhCD-RAP dialyzed into a buffer of pH 6 and pH 8 showed a strong tendency to aggregation. These solutions had a milk like appearance in contrast to glycine (pH 4) where the solution was still showing a non-milky clear like appearance.

rhCD-RAP was concentrated to 30 mg/mL (pH 4.0) and was subsequently stressed by 5 freeze/thaw cycles accordingly. Aggregated rhCD-RAP was removed afterwards by centrifugation and the remaining soluble rhCD-RAP was quantified by UV/Vis. rhCD-RAP solutions at pH 6.0 and pH 8.0 were directly stressed in lower concentrations as a result of filter blocking during the concentration procedure.

FIG. 9 shows the effect of self-stabilizing rhCD-RAP under acidic conditions e.g. under pH 4.0 due to the raising of the net charge of the protein. Although glycine is uncharged at pH 4.0 it was possible to achieve a sufficient solubility of rhCD-RAP.

Whereas in the pH range between pH 6-8 formulations comprising CD-RAP must comprise of charged amino acids as a stabilizing excipient, at lower pH e.g. pH 4.0 rhCD-RAP is able to stabilize itself without the addition of charged amino acids.

EXAMPLE 6

Effect of Histidine in Stabilizing rhCD-RAP

Previous experiments demonstrated charged amino acids as a powerful tool for rhCD-RAP stabilization for high concentrations of up to 30 mg/mL at about neutral pH such as pH 6.0. To determine the range of the identified buffers this Example shows the dependency of the concentration of the buffer component for CD-RAP to be best suitably exemplified for histidine. Therefore, rhCD-RAP was dialyzed into histidine phosphate in the range from 0 mM to 300 mM histidine as shown in Table 5 below. Additionally, these formulations were adjusted to physiological osmolality by the addition of a sufficient amount potassium chloride.

TABLE 5 different concentrations of L-histidine buffers, osmolality before adjustment with potassium chloride to isotonic conditions

| histidine [mM] | potassium chloride [mM] | osmolality [mOsmol/kg] |
| --- | --- | --- |
| 0 | 0 | 2 |
| 0 | 150 | 295 |
| 50 | 0 | 67 |
| 50 | 116.5 | 298 |
| 100 | 0 | 121 |
| 100 | 89.5 | 302 |
| 200 | 0 | 215 |
| 200 | 42.5 | 302 |
| 300 | 0 | 299 | rhCD-RAP was concentrated to 30 mg/mL (pH 6.0) and subsequently stressed by 5 freeze/thaw cycles. Aggregated rhCD-RAP was removed afterwards by centrifugation and the remaining soluble rhCD-RAP was quantified by UV/Vis.

FIG. 10 demonstrates that the solubility of rhCD-RAP in histidine phosphate at pH 6.0 was strictly dependent on the concentration of histidine. Whereas 0 mM histidine at pH 6.0 failed to stabilize rhCD-RAP, higher concentrations led to significantly improved solubility in correlation to the increase of histidine molarity. These repeated freeze/thaw-experiments have shown that buffers comprising L-histidine in concentrations of 200 mmol/l and more provided stable rhCD-RAP solutions at 30 mg/mL.

As seen in Figure 1lthe addition of potassium chloride did not influence the solubility of rhCD-RAP in histidine phosphate. Therefore, an adjustment to isotonic osmolality of a pharmaceutical CD-RAP formulation with potassium chloride can be used without a negative impact on the solubility and stability of rhCD-RAP in high concentrations.

EXAMPLE 7

Inhibition of GDF-5-induced ALP Activity

MCHT cells were seeded in a density of 30,000 cells per well in 96-well plates and were grown overnight in culture medium (alpha-MEM containing glutamine completed with 10% FCS). The next day, stimulation with rhGDF-5 and rhCD-RAP was started by changing culture medium in each well to 160 µl of the particular stimulation medium. All standards and samples were done in quadruplets. A dilution series of rhGDF-5 with the following concentrations of rhGDF-5 (1200 ng/ml, 400 ng/ml, 133.2 ng/ml, 44.5 ng/ml, 14.8 ng/ml rhGDF-5 in complete culture medium) was prepared to achieve a standard curve. For analysis of the rhCD-RAP-mediated inhibition of ALP activity the cells were co-stimulated with 400 ng/ml rhGDF-5 and 1 to 10 µM rhCD-RAP. Cells were cultivated within the stimulation medium for three days before they were lysed by adding 0.2 g MgCl2×6H2O in 2 mL Nonidet P40 and incubating for 16 h in an incubator. 50 µl of the lysate were transferred to a new 96-well-plate and 50 µl substrate buffer (0.222 g PNPP in diethanolamine buffer, Pierce) were added and incubated for 45 min at 37° C. Afterwards the reaction was stopped by adding 0.5 M NaOH. Absorbance was measured at 405 nm in a plate reader. Background ALP activity was measured in untreated cells and was subtracted from all standards and samples. The standard curve was used to calculate the ALP activity in all samples.

EXAMPLE 8

CD-RAP Stimulation of Chondrocytes and Analysis with qRT-PCR

Chondrocytes were isolated from human articular cartilage derived from patients undergoing total knee replacement. Cartilage was cut from the bone and into small pieces. The cartilage pieces were digested with 1% Pronase in DMEM/F12 containing 1% Penicillin/Streptomycin at 37° C. for 1 h. After centrifugation at 200×g for 5 min at room temperature, the cartilage pieces were washed once with PBS. They were digested in 0.07% Collagenase A in culture medium (DMEM/F12 completed with 10% FCS and 1% Penicillin/Streptomycin) at 37° C. overnight. The next day the cell suspension was filtered successively through 100, 70 and 40 µm cell strainers. The cells were spun down, resuspended in culture medium and seeded in 6-well-plates at a density of 250,000 cells per well. The cells were cultivated at 37° C., 5% CO2 and 90% humidity until they reached confluency (about 1 week). Medium was changed every second day.

For the stimulation with CD-RAP, the cells were starved in serum-free medium overnight. CD-RAP (0.5-5 µM) was added in serum-free DMEM/F12 and the cells were cultivated for 24 h. Subsequently, cells were lysed and RNA was extracted with RNeasy Mini Kit according to the manufacturer's instructions. 1 µg RNA was used to prepare cDNA with the QuantiTect Reverse Transcription Kit (Qiagen). RT-PCR was performed with 4 µl diluted cDNA (diluted 1:5), 10 µl QuantiFast SYBR Green PCR Mix (Qiagen), 4 µl nuclease-free water and 2 µl primer-mix, 50 cycles on a Light cycler under standard conditions. The following primers were used: 18SrRNA (Qiagen, QuantiTect Primer Assay QT00199367, MMP13forward GGGTTCCTGATGTGGGTGAATA (SEQ ID No. 5), MMP13reverse GCCATCGTGAAGTCTGGTA (SEQ ID No. 6). The results were normalized to the housekeeper 18S rRNA.

---

What is claimed is:

1. A stable aqueous formulation comprising:
   (i) CD-RAP in an amount in the range of 5 to 30 mg/mL; and
   (ii) arginine phosphate in an amount in the range of 250 to 380 mM and at a pH in the range of 6 to 8, or histidine phosphate in an amount in the range of 50 to 300 mM and at a pH in the range of 6 to 8,
   wherein the CD-RAP protein is directly dissolved therein, wherein the CD-RAP is not encapsulated or entrapped in liposomes, and wherein the CD-RAP does not lose more than 15% of its biological activity during storage relative to an activity of CD-RAP at beginning of storage, wherein storage is at least for one month.

2. The formulation claim 1, which comprises a buffer.

3. The formulation of claim 1, which comprises a tonicity modifier.

4. The formulation of claim 1, which comprises a stabilizer.

5. The formulation of claim 1, which comprises an excipient.

6. The formulation of claim 1 comprising at least 10 mg/mL CD-RAP.

7. The formulation of claim 1, wherein the storage is for at least six months.

8. The formulation of claim 1, wherein the storage is for a period in the range of one month to two years.

9. The formulation of claim 1 wherein storage includes subjecting the formulation to one or more freeze-thaw cycle(s).

10. A kit comprising the formulation of claim 1.

11. A freeze-dried, a lyophilized, or spray-dried formulation comprising CD-RAP and arginine phosphate or histidine phosphate, where, upon addition of water, the formulation is configured to form an aqueous formulation comprising:
    (i) CD-RAP in an amount in the range of 5 to 30 mg/mL; and
    (ii) arginine phosphate in an amount in the range of 250 to 380 mM and at a pH in the range of 6 to 8, or histidine phosphate in an amount in the range of 50 to 300 mM and at a pH in the range of 6 to 8,
    wherein the CD-RAP protein is directly dissolved therein, wherein the CD-RAP is not encapsulated or entrapped in liposomes, and wherein the CD-RAP does not lose more than 15% of its biological activity during storage relative to an activity of CD-RAP at beginning of storage, wherein storage is at least for one month.

12. A method for improving the stability of CD-RAP during a storage period, the method comprising:
    providing a stable aqueous formulation comprising:
      (i) CD-RAP in an amount in the range of 5 to 30 mg/mL; and
      (ii) arginine phosphate in an amount in the range of 250 to 380 mM and at a pH in the range of 6 to 8, or histidine phosphate in an amount in the range of 50 to 300 mM and at a pH in the range of 6 to 8,
      wherein the CD-RAP protein is directly dissolved therein, wherein the CD-RAP is not encapsulated or entrapped in liposomes;
    storing the aqueous formulation for a period of at least for one month, wherein the CD-RAP does not lose more than 15% of its biological activity during the period relative to an activity of CD-RAP at beginning of storage.

13. The method of claim 12 wherein providing comprises adding water to a freeze-dried, a lyophilized, or spray-dried formulation comprising CD-RAP and arginine phosphate or histidine phosphate.

14. The method of claim 12 wherein the period during storing is for at least six months.

15. The method of claim 12 wherein the period during storing is in the range of one month to two years.

16. The method of claim 12 wherein during storing the formulation is subjected to one or more freeze-thaw cycle(s).

* * * * *